US012778711B2

(12) United States Patent
Sariibrahimoglu et al.

(10) Patent No.: US 12,778,711 B2
(45) Date of Patent: Nov. 3, 2026

(54) MEDICAL IMPLANTS FOR MARKING SURGICAL SITES

(71) Applicant: Tepha, Inc., Lexington, MA (US)

(72) Inventors: Kemal Sariibrahimoglu, Waltham, MA (US); Skander Limem, Lynnfield, MA (US); Said Rizk, Windham, NH (US); Simon F. Williams, Cambridge, MA (US)

(73) Assignee: Tepha, Inc., Lexington, MA (US)

( * ) Notice: Subject to any disclaimer, the term of this patent is extended or adjusted under 35 U.S.C. 154(b) by 735 days.

(21) Appl. No.: 17/917,330

(22) PCT Filed: Mar. 29, 2021

(86) PCT No.: PCT/US2021/024728
§ 371 (c)(1),
(2) Date: Oct. 6, 2022

(87) PCT Pub. No.: WO2021/206948
PCT Pub. Date: Oct. 14, 2021

(65) Prior Publication Data

US 2023/0149117 A1 May 18, 2023

Related U.S. Application Data

(60) Provisional application No. 63/005,927, filed on Apr. 6, 2020.

(51) Int. Cl.
*A61B 90/00* (2016.01)
*A61B 17/00* (2006.01)

(52) U.S. Cl.
CPC .... *A61B 90/39* (2016.02); *A61B 2017/00004* (2013.01); *A61B 2017/00867* (2013.01); *A61B 2090/3908* (2016.02); *A61B 2090/3937* (2016.02); *A61B 2090/3966* (2016.02)

(58) Field of Classification Search
CPC .......... A61B 90/39; A61B 2017/00004; A61B 2090/3966
See application file for complete search history.

(56) References Cited

U.S. PATENT DOCUMENTS

2004/0078079 A1* 4/2004 Foley ...................... A61F 2/447 623/17.11
2005/0060025 A1* 3/2005 Mackiewicz ............. A61F 2/91 623/1.34
2008/0249638 A1* 10/2008 Asgari ...................... A61F 2/28 623/23.72
2008/0312733 A1* 12/2008 Jordan ...................... A61F 2/88 623/1.21
2010/0004725 A1 1/2010 Zipse et al.
2010/0234726 A1 9/2010 Sirimanne et al.
2010/0300045 A1* 12/2010 Sarac ..................... A61B 50/30 53/428
2012/0259405 A1 10/2012 Weber et al.
2013/0289389 A1* 10/2013 Hermann ............. A61N 5/1015 600/424
2013/0289390 A1 10/2013 Hermann et al.
2013/0319603 A1 12/2013 Wu
2014/0316508 A1 10/2014 Thompson et al.
2015/0118152 A1* 4/2015 Ganatra .................. A61L 27/18 524/21
2015/0374517 A1* 12/2015 Majercak .................. A61F 2/90 623/1.13
2016/0082286 A1 3/2016 Stubbs et al.
2019/0099618 A1 4/2019 Stauffer et al.
2019/0209354 A1* 7/2019 Scanlon .................. A61F 2/915
2019/0328556 A1 10/2019 Eubanks et al.

FOREIGN PATENT DOCUMENTS

CN 107638231 A 1/2018
CN 109172044 A 1/2019
JP 2006-516217 A 6/2006

OTHER PUBLICATIONS

International Search Report and Written Opinion mailed Sep. 2, 2021 for International Application No. PCT/US2021/024728.
International Preliminary Report on Patentability mailed Oct. 20, 2022 for International Application No. PCT/US2021/024728.
Extended European Search Report mailed Sep. 11, 2025 for International Application No. EP25183269.7.

* cited by examiner

*Primary Examiner* — Andrew S Rosenthal
(74) *Attorney, Agent, or Firm* — Wolf, Greenfield & Sacks, P.C.

(57) ABSTRACT

Implantable fiducial marker devices with a predefined shape can deform when stress is applied in vivo, and recover their shape when stress is removed reduce patient discomfort and palpability. The devices can be used to mold irregular tumor resection cavities into a more ideal shape for radiation therapy allowing more accurate treatment. After treatment, the devices resorb eliminating unnecessary testing that occurs when clinicians are unaware of implanted fiducial marker devices. Tissue ingrowth into the devices can also result in improved cosmetic outcomes when the devices are implanted in the breast after a lumpectomy. The devices preferably comprise poly-4-hydroxybutyrate or poly(butylene succinate) or copolymers thereof.

33 Claims, 6 Drawing Sheets

MEDICAL IMPLANTS FOR MARKING SURGICAL SITES

CROSS-REFERENCE TO RELATED APPLICATIONS

This application is a national stage filing under 35 U.S.C. § 371 of International Application No. PCT/US2021/024728, filed Mar. 29, 2021, which claims the benefit under 35 U.S.C. 119(e) of U.S. Provisional Application No. 63,005,927, filed Apr. 6, 2020, each of which is hereby incorporated by reference in its entirety.

FIELD OF THE INVENTION

The present invention generally relates to the field of surgery, and more particularly, the invention relates to medical implants that can be used to delineate the margins of surgical sites during radiation therapy.

BACKGROUND OF THE INVENTION

Radiation therapy is often performed following the removal of a tumor to destroy remaining cancer cells, and lower the risk of cancer recurrence. However, delineating the tissue margins of a tumor cavity postoperatively for radiation therapy can be difficult. Traditionally, clinicians have relied upon the surgical scar site or the presence of seroma to identify the site for radiation therapy and the radiation target volume. However, these identification methods are not the most accurate, and cannot only reduce the effectiveness of radiation therapy but can also increase the chances that healthy tissue surrounding the cavity will be damaged. Correctly locating the margins of a tumor resection cavity can also be extremely difficult because the cavity may have an irregular shape, and in some tissues the shape can change over time. For example, the tumor cavity may grow or shrink during respiration, or may even change in size and shape as a result of continued radiation therapy treatments.

To address these issues, clinicians often use fiducial marker devices to better define the location of the cavity, and provide a clearer target for external radiation beam treatment. A fiducial marker device is a marker or set of markers placed in an imaging field as a point of reference. It can be used in planning target volume (PTV) for radiation treatment and for targeting a specific location and shape in the body. The PTV is determined by measurement of the gross tumor volume (GTV), adding a margin for disease spread that cannot be fully imaged to arrive at a clinical target volume (CTV), and further adding an additional margin around the CTV to ensure that the radiation therapy is actually delivered to the CTV.

The first fiducial markers were typically small metal objects, for example, metal clips or pellets, used in the treatment of breast, abdominal, liver, lung, and prostate cancers. While these small metal objects can be beneficial as fiducial markers, they have been known to migrate resulting in larger than necessary target volumes for radiation therapy. Their ability to accurately define the volume of a tumor resection cavity, which may have an irregular shape, can also be a limitation.

To more precisely locate the radiation target volume following tumor resection, and prevent migration of metal clips, three-dimensional fiducial markers have been disclosed.

US Patent Application No. 20090024225 to Stubbs discloses a bioabsorbable three-dimensional spherical implantable fiducial marker that has a lower density than soft tissue to allow it to be imaged postoperatively. The density of the bioabsorbable material used to prepare the marker is 1.03 g/cc or less.

U.S. Pat. Nos. 9,014,787 and 9,199,092 to Stubbs disclose rigid bioabsorbable three-dimensional fiducial markers containing metallic elements that have arms emanating from the center of the device.

U.S. Pat. Nos. 9,615,915 and 9,980,809 to Lebovic, U.S. Pat. No. 10,500,014 to Hermann, and US Patent Application Nos. 20130289389 and 20130289390 to Hermann disclose three-dimensional fiducial marker devices that comprise an absorbable material and radiographically visible elements to visualize the device when it is placed in a surgical resection cavity.

Wiens, N. et al. Effect of BioZorb® surgical marker placement on post-operative radiation boost target volume, J Radiat Oncol, 7:175-179, (2018) discloses a three-dimensional helical fiducial marker with six metal clips. The marker is a rigid device made from polylactic acid. Srour and Chung, Utilization of BioZorb implantable device in breast-conserving surgery, Breast J. 2019; 00:1-6 evaluated the palpability of this fiducial marker in the breast, and discovered that the marker continues to be palpable in the breast for years after placement. They reported the presence of the marker in the body 2.8 years after implantation, and that the marker still remained palpable. Palpability of this device is particularly problematic in the treatment of breast cancer for several reasons. First, the presence of the marker device in the breast can be painful and it can cause discomfort particularly if any stress or tension is placed on the breast. The BioZorb device is manufactured from polylactic acid, a polymer with a modulus of elasticity greater than 3 GPa that makes the device rigid so that it will not deform under stress and recover its original shape. Srour and Chung 2019 have disclosed that the presence of the BioZorb device was sufficiently painful in one patient that it needed to be surgically removed. Second, the long-term presence of a foreign mass in a patient's breast can cause anxiety, particularly in breast cancer patients. Third, clinicians that are unaware that the device has been implanted in the breast may subject the patient to unnecessary testing in order to investigate the foreign mass, and as a result raise patient anxiety. Srour and Chung 2019 reported that clinicians ordered additional imaging in 8.8% of patients examined because they were unaware of the marker device. Fourth, the slow resorption and long-term palpability of the device could limit the clinician's ability to detect breast cancer recurrence. See also U.S. Pat. No. 10,500,014 to Hermann, and U.S. Pat. No. 9,014,787 to Stubbs.

Notwithstanding the above, there is still a need for three-dimensional fiducial markers as described herein that can be used to model the surrounding surgical margins of an irregularly shaped tumor cavity into a more defined volumetric shape to provide a clear target for radiation therapy. In particular, there is a need to develop three-dimensional fiducial markers that degrade faster in vivo. Such markers would ideally not be palpable when implanted in the breast, would have a lower modulus of elasticity than existing fiducial markers so that they can deform under stress or tension, and would not cause pain after implantation. There is also a need to develop fiducial markers that would allow tissue in-growth to fill the tumor cavity void space. These markers would be particularly desirable in the treatment of the breast since tissue in-growth into the void space of the tumor resection cavity would provide an improved cosmetic outcome. There is also a further need to develop three-dimensional fiducial markers comprising one or more bio-active agents, such as a chemotherapeutic agent, anti-neoplastic agent, immunomodulator, hormonal agent, anti-angiogenesis agent, antibiotic, radiosensitizer, and an immune-therapeutic agent. The fiducial markers could be used in the treatment of cancer of soft tissues, including the treatment of breast, abdominal, liver, muscle, kidney, lung and prostate cancer.

SUMMARY OF THE INVENTION

Resorbable three-dimensional fiducial markers are described herein that can be used to provide a more precise delivery of radiation therapy to the tissue margins of a tumor resection cavity by conforming the irregular shape of a tissue resection cavity to the shape of the marker. In embodiments, the fiducial marker is formed in a predefined shape that is desirable for radiation therapy, and implanted in a tumor resection cavity to mold the shape of the cavity into a more ideal shape for radiation therapy, such as a spherical or ellipsoid shape. The fiducial markers allow the volume of a tumor resection cavity to be more accurately defined, and targeted during radiation therapy. The fiducial markers reduce the dose of radiation received by normal tissue surrounding the tissue resection cavity, and decrease the size of the margins around the cavity that need to be treated with radiation.

In embodiments, the fiducial marker is not palpable 1, 2, 3, 4, 5, 6, 7, 8, 9, 10, 11 or 12 months after implantation, particularly in the breast of a patient. In embodiments, the fiducial marker is not palpable immediately following implantation, particularly in the breast of a patient. In embodiments, the predefined shape of the fiducial marker is deformed under stress or tension. In embodiments, the predefined shape of the fiducial marker is flexible or compressible, and the shape is not rigid. In embodiments, the predefined shape of the fiducial marker is deformed under stress or tension, and recovers its predefined shape when the stress or tension is removed. Recovery of the predefined shape when stress or tension is removed allows the marker to be used to accurately demarcate the target volume for radiation therapy. The ability of the fiducial marker to deform under stress or tension decreases or eliminates the palpability of the marker, particularly in the breast. The ability of the fiducial marker to deform in the breast under stress or tension also reduces or eliminates the possibility of the device causing pain in the breast. In embodiments, the fiducial marker devices have a modulus of elasticity of less than 50 MPa, and more preferably less than 10 MPa, but greater than 0.5 kPa.

The fiducial marker has a predefined shape with an outer region defining the peripheral boundary of the device. In embodiments, the outer region of the three-dimensional marker is defined by convex surfaces. In embodiments, the peripheral boundary of the marker is defined by a spherical, helical, ellipsoid, scalene ellipsoid, cylindrical, prolate spheroid or oblate spheroid shapes. In other embodiments, the peripheral boundary of the marker is defined by a parallelepiped shape or oval shape. In embodiments, the marker device comprises a three-dimensional framework, skeleton or scaffold that defines its predefined shape and the outer region of the device. In embodiments, the three-dimensional framework, skeleton or scaffold may be an elliptical spiral, spherical spiral, cylindrical spiral, or other spiral that defines an outer region. In other embodiments, the three-dimensional framework, skeleton or scaffold defining the outer region of the fiducial marker may be a skeletal polyhedron, skeletal sphere, skeletal ellipsoid, skeletal cylinder or skeletal parallelepiped.

In embodiments, the outer region of the fiducial marker defining the boundary of the device may have a longitudinal axis with first and second ends and a length (l), and a diameter (d) or width (w) at the midpoint of the longitudinal axis between the first and second ends. In embodiments, the length (l) of the marker is 1 to 6 cm, and the diameter (d) or width (w) is 1 to 5 cm. In these embodiments, the marker may have dimensions, for example, of (l)×(d) of 2×2 cm, 2×3 cm, 3×3 cm, 3×4 cm, 4×4 cm, 4×5 cm. In other embodiments, the outer region of the fiducial marker defining the boundary of the device may have a longitudinal axis with first and second ends and a length (l), and a width (w) and height (h) at the midpoint of the longitudinal axis between the first and second ends. In these other embodiments, the length (l) of the marker is 1 to 4 cm, the width (w) of the marker is 1 to 3 cm, and the height (h) of the marker is 1 to 2 cm. In these other embodiments, the marker may have dimensions, for example, of (l)×(w)×(h) of 3×2×1 cm, 3×3×1 cm, 1×1×2 cm, 2×1×2 cm, and 1×2×2 cm.

In embodiments, the fiducial marker is porous or has an open framework, skeleton or scaffold to allow tissue in-growth. In embodiments, the fiducial marker has a porous structure to allow tissue in-growth. Tissue in-growth can help to secure the device in place, and fix the position of the visualization markers on the device. In embodiments, the fiducial marker maintains its predefined shape, or can assume its predefined shape in the absence of stress or tension, until tissue in-growth into the device has secured the visualization markers in place. Tissue in-growth can also fill the void space of a tumor resection cavity, and in some treatments, such as breast cancer, result in an improved cosmetic outcome. In embodiments, the fiducial marker can be used as a void filler.

In embodiments, the fiducial marker is used as an oncoplastic device. In embodiments, the fiducial marker is used to reliably mark a surgical site. In embodiments, the fiducial marker is used to define a planning target volume (PTV) for radiation therapy. The fiducial marker may also be used for radiographic disease surveillance.

In embodiments, the fiducial marker comprises a plurality of visualization markers. The visualization markers can be used to determine the planning target volume (PTV) for radiation therapy, and to focus the radiation on the target site. The visualization markers provide high contrast when tissue containing the marker is imaged. The visualization markers can be imaged by one or more of the following methods: ultrasound, X-Ray, MRI (magnetic resonance imaging), CT (computerized tomography) or mammography. In embodiments, the visualization markers are made from titanium, stainless steel, gold, or a composite polymer material, for example, a polymer mixed with barium sulfate. In embodiments, visualization markers are coated with a hydrogel. In embodiments, the visualization markers are radio-opaque clasps that are attached to the outer region of the fiducial marker to provide an imagable three-dimensional target. In embodiments, the visualization markers are attached to the outer region of the fiducial marker in order to prevent migration of the clasps, and radiation of larger volumes than is necessary. In embodiments, visualization markers are placed at the first and second ends of the longitudinal axis of the device so its length (l) can be imaged in vivo, and they are also placed around the periphery at the midpoint of the longitudinal axis between the first and second ends so its diameter or width can be imaged.

In embodiments, the predefined shape of the fiducial marker, or the framework of the fiducial marker, is formed from a radiolucent material. In other embodiments, the predefined shape of the fiducial marker, or the framework of the fiducial marker, is formed from a radio-opaque material or from both radiolucent and radiopaque materials.

In embodiments, the fiducial marker has an integral radiographic visualization property.

The predefined shape of the fiducial marker is resorbable. In embodiments, the visualization markers attached to the predefined shape or incorporated into the predefined shape are either permanent or resorbable.

In embodiments, the predefined shape of the fiducial marker is resorbable. In embodiments, the resorbable fiducial marker maintains its predefined shape, in the absence of stress or tension, in vivo long enough for radiation therapy treatment to be completed. In embodiments, the fiducial marker maintains its predefined shape, or can assume its predefined shape in the absence of stress or tension, for a period of 1, 2, 3, 4, 5, 6, 7, 8 or 9 months following implantation. In embodiments, the predefined shape of the fiducial marker is resorbed in vivo in less than 24, 23, 22, 21, 20, 19, 18, 17, 16, 15, 14, 13, 12, 11, 10 or 9 months following implantation. Resorption of the predefined shape obviates the need to perform a secondary surgical intervention to remove the marker. Resorption also eliminates the possibility that the device can cause any pain or discomfort, eliminates the possibility that clinicians unaware of the device will order unnecessary testing to investigate its presence, and eliminates any patient anxiety due to the presence of the marker, particularly in the breast of a cancer patient.

In embodiments, the three-dimensional framework, skeleton or scaffold of the fiducial marker can be formed with one or more filaments, and can optionally incorporate one or more struts.

In embodiments, the fiducial marker comprises polymeric struts, fibers, coils or springs that have one or more of the following properties: (i) diameters of 0.025 to 3 mm, more preferably 0.1 to 2 mm, and even more preferably 0.15 to 1 mm; (ii) breaking loads of 0.1 to 200 N, more preferably 1 to 100 N, and even more preferably 2 to 50 N; (iii) elongation at break values of 22% to 1,000%, and more preferably 100% to 700%; and (iv) elastic modulus values of 0.05 to 3 GPa, more preferably 0.1 to 1 GPa, and even more preferably 0.2 to 0.8 GPa. In embodiments, the fiducial markers comprise unit cells formed from polymeric struts, fibers, coils or springs with these properties. In embodiments, the unit cells are part of a framework, skeleton or scaffold of the fiducial marker. In embodiments, the unit cells may have the same properties, or different properties. In embodiments, the polymeric struts, fibers, coils or springs are resorbable. In embodiments, the fiducial marker has an elastic modulus of less than 50 MPa, more preferably less than 10 MPa, but greater than 0.5 kPa, and is formed from polymeric struts, fibers, coils or springs that have one or more of the following properties: (i) diameters of 0.025 to 3 mm, more preferably 0.1 to 2 mm, and even more preferably 0.15 to 1 mm; (ii) breaking loads of 0.1 to 200 N, more preferably 1 to 100 N, and even more preferably 2 to 50 N; (iii) elongation at break values of 22% to 1,000%, and more preferably 100% to 700%; and (iv) elastic modulus values of 0.05 to 3 GPa, more preferably 0.1 to 1 GPa, and even more preferably 0.2 to 0.8 GPa.

In embodiments, the fiducial tissue marker device comprises a resorbable porous scaffold with a 3D predefined shape defining the periphery of the device, wherein the predefined shape can be deformed under stress and recover its shape when the stress is removed, and wherein the scaffold comprises visualization markers in discrete locations on the periphery of the device. In embodiments, the fiducial marker device has a 3D predefined shape, and has shape memory.

In embodiments, the predefined shape of the fiducial marker is formed from a resorbable polymer. A resorbable polymer can be used to form a three-dimensional framework, skeleton or scaffold that defines the outer region of the fiducial marker and its predefined shape. In embodiments, the predefined shape or framework of the fiducial marker is formed from poly-4-hydroxybutyrate (P4HB) or copolymer thereof, or from poly(butylene succinate) (PBS) or copolymer thereof.

In embodiments, the fiducial marker is prepared by 3D printing, including melt extrusion deposition, fused filament fabrication, fused pellet deposition, selective laser melting, printing of slurries and solutions using a coagulation bath and printing using a binding solution and powders or granules. In embodiments, the fiducial marker is prepared by injection molding, and by injection molding with multipart molds.

In embodiments, the fiducial markers can be fixated in a tumor bed, or surgical resection cavity, using permanent suture, resorbable suture, staples or by other fixation means. Fixation helps to prevent any subsequent migration of the device. In embodiments, the fiducial markers comprise one or more suture eyelets to fixate the devices in place. Suture may be passed through the eyelets and fixated to tissue in order to prevent migration of the devices after implantation.

In embodiments, the fiducial marker is implanted after a lumpectomy, used in planning target volume (PTV) for radiation therapy, and delivery of post-operative radiation boost to the breast.

In embodiments, the fiducial marker contains one or more of the following: a chemotherapy agent, an anti-neoplastic agent, an anti-angiogenesis agent, an immunomodulator, a hormonal agent, an immune-therapeutic agent, an antibiotic, and a radio-sensitizing agent.

In embodiments, polymers used to prepare the fiducial implants have weight average molecular weights of 50 to 1,000 kDa, more preferably 90 to 600 kDa, and even more preferably from 200 to 450 kDa.

In embodiments, the fiducial marker implants have an endotoxin content of less than 20 endotoxin units per implant. In embodiments, the fiducial makers are sterilized by ethylene oxide, electron beam, or gamma-irradiation.

In embodiments, the fiducial markers can be used in the treatment of cancer of soft tissues, including the treatment of breast, abdominal, liver, muscle, kidney, lung and prostate cancer.

In embodiments, a method of implanting a fiducial marker device comprises: creating a cavity in a patient by removing soft tissue through an open surgical incision from a location within the body; inserting, into the cavity, a fiducial marker device having a resorbable porous scaffold with a predefined shape defining the periphery of the device, wherein the predefined shape has shape memory; and closing the surgical site. The method may further comprise suturing the device in the cavity. Optionally, the creating step is performed in the breast of the patient, and the device is implanted in the cavity in the breast of the patient. In a preferred embodiment, method includes creating the cavity during a lumpectomy procedure.

In embodiments, a method comprises determining a planning target volume (PTV) for radiation treatment of a patient based on the fiducial marker device implanted in the patient.

In embodiments, a method comprises forming the fiducial marker device by 3D printing.

In embodiments, the method forms the fiducial marker device based on a 3D model, and optionally, comprising the steps of generating the 3D model based on image data from the patient. Examples of image data include 3D image data arising from CT or MRI scans. Indeed, embodiments include generating 3D image data of a tumor or lesion or tissue volume and creating (optionally 3D printing) the fiducial marker device based on the 3D image data.

In embodiments, a physician customizable fiducial marker kit comprises: at least one fiducial marker device comprising a 3D body, and a plurality of fixed, spaced-apart, visualization marker engagement features; and a plurality of visualization markers, each comprising a mating feature for connecting to the visualization marker engagement feature such that one or more of visualization markers may be secured to the 3D body of the fiducial marker device as desired by the physician.

In embodiments, the visualization marker engagement feature is a hole, and the visualization marker mating feature is a post.

In view of the foregoing, it is thus an object of the invention to provide resorbable fiducial markers.

It is still another object of the invention to provide fiducial markers that are not palpable and do not cause pain after implantation.

It is yet another object of the invention to provide methods to manufacture fiducial markers that are pliable and that do not cause pain after implantation.

It is still another object of the invention to provide methods to implant the fiducial markers.

These and other objects, aspects, and advantages of the subject invention shall become apparent in view of the following description with reference to the accompanying figures.

DETAILED DESCRIPTION OF THE INVENTION

Figure 1A:
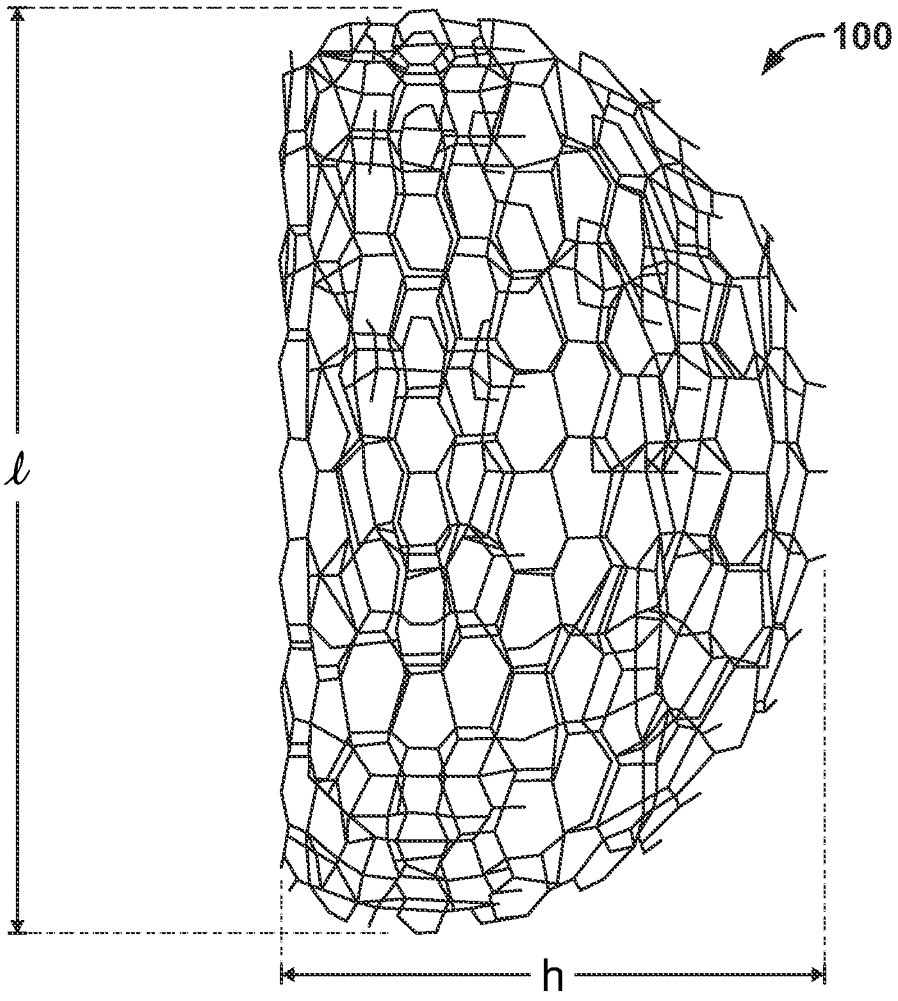
FIGS. 1A-1B show respectively a front view and an isometric view of a porous fiducial marker device (100) with an open porous honeycomb scaffold structure in accordance with an embodiment of the invention. The device (100) has an ellipsoid, spherical shape with a base diameter or length (l) and a height (h) shown in FIG. 1A.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

In embodiments of the invention, a resorbable three-dimensional fiducial marker is implanted in a tumor resection cavity, molds the cavity to form a target volume for radiation therapy with more precisely demarcated tissue margins, decreases the size of the tissue margins around the cavity that need to be irradiated, reduces the exposure of healthy tissue to radiation, deforms in vivo under stress or tension so it is not palpable or a source of pain, and resumes its original shape in vivo during the period of radiation therapy when stress or tension is removed. The fiducial marker is sized for use in different sized tumor resection cavities. The fiducial marker is porous, and allows tissue in-growth. In embodiments, the fiducial marker has an internal scaffold structure that encourages tissue in-growth. Tissue in-growth secures the device in place, and can also provide an improved cosmetic outcome by filling a tissue void space. After radiation therapy, the three-dimensional structure of the fiducial marker is resorbed.

In embodiments, the implant comprises an outer surface or peripheral structure (e.g., a shell), and an internal organized architecture which can support the peripheral structure and provide an interconnected porous structure.

In embodiments, the fiducial marker has a predefined three-dimensional shape that is not palpable after implantation, particularly in the breast of a patient. When stress or tension is applied to the fiducial marker in vivo, the marker deforms, and resumes its predefined shape when the stress or tension is removed, for example, during imaging. In embodiments, the fiducial marker has shape memory allowing the fiducial marker to deform from a predefined shape when a stress is applied and resume its predefined shape when the stress is removed. In preferred embodiments, the marker is flexible, not rigid like existing fiducial marker devices, and can be compressed. After compressive forces are removed, the marker returns to its predefined shape. In embodiments, the fiducial marker has a modulus of elasticity of less than 50 MPa, more preferably less than 10 MPa, and even more preferably less than 1 MPa that allows the device to be deformed and recover its original shape.

In embodiments, the fiducial marker has a predefined three-dimensional shape with a longitudinal axis with first and second ends, and a diameter or width at the mid-point between the first and second ends. The fiducial marker has a three-dimensional outer region that defines the periphery of the device. When implanted in a tumor resection cavity, the outer region molds the cavity into a shape such that the tissue margins of the shape can be easily irradiated. In embodiments, the outer region is shaped so that the periphery of the device has a spherical, ellipsoid, scalene ellipsoid, cylindrical, prolate spheroid, oblate spheroid, oval, or parallelepiped shape. In embodiments, the outer region of the fiducial marker is formed from a framework, skeleton or scaffold. In embodiments, the framework, skeleton or scaffold is formed from one or more filaments, and can optionally incorporate one or more struts. In embodiments, the framework, skeleton or scaffold may be a spiral or helix that defines the peripheral boundary of the marker, including an elliptical spiral, spherical spiral, cylindrical spiral, or a skeletal polyhedron, skeletal sphere, skeletal ellipsoid, skeletal cylinder or skeletal parallelepiped.

In embodiments, the fiducial marker is porous, or is an open framework, skeleton or scaffold that allows tissue in-growth into the fiducial marker. Tissue in-growth fixates the device in the tumor bed so that it cannot migrate, and the visualization markers are secured at the margins of the resected cavity. In embodiments, the three-dimensional structure of the fiducial marker degrades after tissue in-growth has secured the visualization markers in place.

In embodiments, the fiducial marker also serves as a void filler. Tissue in-growth into the void of the tumor resection cavity can provide an improved cosmetic outcome in the treatment of certain cancers, such as breast cancer, by eliminating visible defects.

In embodiments, the fiducial marker comprises a plurality of visualization markers that are placed on the marker so that the volume of the marker can be imaged after implantation, used to plan the radiation target volume, and used to focus radiation on the target site. The visualization markers are radio-opaque, and in embodiments are fastened to the outer region of the fiducial marker to allow visualization of the outer region of the marker. Attachment of the visualization markers to the outer region of the marker prevents the visualization markers from migrating. In embodiments, the visualization markers can be imaged by one or more of the following methods: ultrasound, X-Ray, MRI, CT, mammography, positron emission tomography, and single-photon emission computed tomography.

In embodiments, the visualization markers are made from titanium, stainless steel, gold or a composite polymer material such as a polymer mixed with barium sulfate.

In embodiments, the visualization markers or devices are coated with hydrogels. Hydrogels can be used to improve the visibility of the device. Preferably, the hydrogels are absorbable.

In embodiments, the fiducial marker further comprises one or more suture eyelets. Suture eyelets can be used to fixate the marker in the tumor resection cavity by suturing the device in place. The eyelets may also make it easier to mold the tumor resection cavity to the shape of the marker.

In embodiments, the integrity of the three-dimensional structure of the fiducial marker remains intact during the period of radiation therapy, but degrades thereafter. After degradation of the three-dimensional structure, only non-degradable visualization markers remain in vivo. In embodiments, the three-dimensional structure of the fiducial marker is resorbed in vivo in less than 6-24 months. A second procedure to remove the fiducial marker after radiation therapy is not required.

In embodiments, the three-dimensional shape of the fiducial marker comprises a resorbable polymer. In embodiments, the three-dimensional shape comprises P4HB or copolymer thereof, or PBS or copolymer thereof.

In embodiments, the fiducial marker may comprise one or more of the following: a chemotherapy agent, an anti-neoplastic agent, an anti-angiogenesis agent, an immunomodulator, a hormonal agent, an immune-therapeutic agent, an antibiotic, and a radio-sensitizing agent.

In embodiments, the three-dimensional shape of the fiducial marker is 3D printed. In embodiments, the marker is 3D printed from a composition comprising a resorbable polymer. In embodiments, the three-dimensional shape of the fiducial marker is prepared by injection molding, including injection molding using a multipart mold.

In embodiments, the fiducial marker is used in radiation treatment for patients with cancer of soft tissues, including the treatment of breast, abdominal, liver, muscle, kidney, lung and prostate cancer. In a preferred embodiment, the fiducial marker is used in the treatment of breast cancer, and is implanted after lumpectomy to facilitate radiation boost treatments of the breast.

In embodiments, the implanted fiducial marker is sutured in place in vivo to prevent it from migrating. The marker may be sutured in place with resorbable or permanent suture. These sutures may be monofilament or multifilament.

I. Definitions

"Bioactive agent" is used herein to refer to therapeutic, prophylactic or diagnostic agents, preferably agents that promote healing and the regeneration of host tissue, and also therapeutic agents that prevent, inhibit or eliminate infection. "Agent" includes a single such agent and is also intended to include a plurality.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer formed of two or more different monomers.

"Clinical target volume" or "CTV" as used herein means the volume containing the gross tumor volume (GTV), plus a margin around the GTV for spread of disease that cannot be fully imaged.

"Copolymers of poly(butylene succinate)" as generally used herein means any polymer containing 1,4-butanediol units and succinic acid units with one or more different diols, diacid or hydroxycarboxylic acid units, including hydroxycarboxylic acid groups with one or more carboxylic acid or hydroxy acid groups. The copolymers may also comprise chain extenders, coupling agents, cross-linking agents or branching agents.

"Copolymers of poly-4-hydroxybutyrate" as generally used herein means any polymer containing 4-hydroxybutyrate with one or more different hydroxy acid units.

"Drop ratio" as used herein means the ratio of the drop width to the drop height during 3D printing.

"Elongation at break" as used herein means the increase in length of a material that occurs when tension is applied to break the material. It is expressed as a percentage of the material's original length.

"Endotoxin units" as used herein are determined using the limulus amebocyte lysate (LAL) assay as further described by Gorbet et al. Biomaterials, 26:6811-6817 (2005).

"Gross tumor volume" or "GTV" as used herein means the extent of the tumor that can be imaged, palpated or seen.

"Macro-porous" materials or structures as used herein have average pore size diameters of at least 25 microns, more preferably at least 50 microns, and even more preferably at least 75 microns.

"Molecular weight" as used herein, unless otherwise specified, refers to the weight average molecular weight (Mw), not the number average molecular weight (Mn), and is measured by GPC relative to polystyrene.

"Oriented" as generally used herein refers to molecular alignment of polymer chains in a material. A polymer that has been stretched becomes partly oriented and then highly oriented, and the tensile strength increases with increasing orientation. For example, an unoriented polymeric fiber may be stretched to orient the fiber which results in a polymeric fiber with higher tensile strength.

"Planning target volume" or "PTV" as used herein means the volume that will be treated by, for example, radiation therapy. The PTV can be determined from measurement of the gross tumor volume (GTV), adding a margin for disease spread that cannot be fully imaged to arrive at a clinical target volume (CTV), and further adding an additional margin to the CTV to ensure that the radiation therapy is actually delivered to the CTV.

"Poly-4-hydroxybutyrate" as generally used herein means a homopolymer containing 4-hydroxybutyrate units. It can be referred to herein as Tepha's P4HB™ polymer or TephaFLEX® biomaterial (manufactured by Tepha, Inc., Lexington, MA).

"Poly(butylene succinate)" as generally used herein means a polymer containing 1,4-butanediol units and succinic acid units. It may be abbreviated as "PBS".

"Radiation therapy" as generally used herein means a cancer treatment using an external beam of intense energy, such as for example X-rays or protons, to kill cancer cells.

"Radiopaque" as used herein refers to structures or materials that resist the passage of x-rays.

"Resorbable" as generally used herein means the material is degraded in the body, and the degradation products are eliminated or excreted from the body. The terms "absorbable", "resorbable", "degradable", and "erodible", with or without the prefix "bio", can be used interchangeably herein, to describe materials broken down and gradually absorbed, excreted, or eliminated by the body.

"Tissue margin" as generally used herein means for example a rim of tissue surrounding a tumor.

II. Materials for Preparing Fiducial Markers

In accordance with embodiments of the invention described herein, implantable medical devices, namely fiducial markers comprising three-dimensional resorbable structures, have a predefined shape that can deform when stress or tension is applied in vivo, and recover their predefined shape when stress or tension is removed. The ability of the marker devices to deform eliminates the pain associated with more rigid fiducial marker devices, and palpability. In embodiments, the fiducial marker devices have a modulus of elasticity of less than 50 MPa, more preferably less than 1 MPa, and even more preferably less than 100 kPa, but greater than 0.5 kPa. These properties are designed to allow the fiducial marker to be deformed elastically under compression or tension.

The three-dimensional shape of the markers also degrades more rapidly in vivo helping to reduce the possibility that the marker can cause pain or discomfort in the patient, and also eliminating the possibility that clinicians unaware of the marker will order unnecessary testing to characterize the foreign body, which can increase patient anxiety.

In embodiments, the fiducial markers allow tissue in-growth into the marker devices after implantation. Tissue in-growth secures the location of visualization markers on the device, but may also fill void space left by a tumor. Filling void space can result in improved cosmetic outcomes for the patient, particularly in the treatment of breast cancer.

In embodiments, the fiducial marker has an outer region that defines the peripheral boundary of the device. In embodiments, the peripheral boundary of the device has a spherical, spheroid, ellipsoid, cylindrical, parallelepiped shape, or shape with convex surfaces. In embodiments, the outer region is formed from a resorbable three-dimensional structure. In embodiments, the three-dimensional structure is a framework, skeleton or scaffold. In embodiments, the framework, skeleton or scaffold comprises one or more filaments. The framework, skeleton or scaffold may also comprise struts. In embodiments, the framework, skeleton or scaffold is a spiral or polyhedron that defines the outer region. In embodiments, the fiducial marker has a scaffold structure. The scaffold structure has an open porous architecture that is designed to encourage tissue in-growth.

In embodiments, the fiducial marker is implanted in a tumor resection cavity, and molds the shape of the cavity to the shape of the peripheral boundary of the marker device defined by its outer region. The molded shape of the tumor cavity formed by the fiducial marker has more clearly demarcated tissue margins that can be more easily irradiated than the irregular shape of a tumor resection cavity, decreases the tissue margins that need to be irradiated, and reduces the unnecessary exposure of healthy tissue to radiation.

In embodiments, the fiducial markers comprise a plurality of visualization markers. The visualization markers are fixed to or incorporated into the three-dimensional structure of the device in a manner that allows the clinician to determine the planning target volume, irradiate the planning target volume, and, if necessary, continue radiographic disease surveillance. The visualization markers are preferably radiopaque, and provide high contrast when the fiducial marker is imaged. In embodiments, the visualization markers are attached to the outer region of the fiducial marker in order to provide an imagable three-dimensional view of the tissue resection cavity, and to prevent the visualization markers from migrating from their implant location. The latter could result in a larger volume of tissue being irradiated than is necessary.

In embodiments, the three-dimensional structure of the fiducial marker comprises a resorbable polymer. In embodiments, the resorbable polymer degrades in vivo in less than 6-24 months. In embodiments, the resorbable polymer is a thermoplastic polymer. In embodiments, the resorbable polymer degrades after radiation therapy has been completed. In embodiments, the resorbable polymer degrades after tissue in-growth, and the visualization markers of the fiducial marker have been secured in place. In embodiments, the resorbable polymer allows the predefined shape of the fiducial marker to be deformed in the presence of stress or tension, and recover its predefined shape when stress or tension is removed. In embodiments, the resorbable polymer is flexible, compressible or elastomeric. In embodiments, the outer region of the fiducial marker is a three-dimensional structure, wherein the three-dimensional structure is a framework, skeleton or scaffold, and the framework, skeleton or scaffold is formed from a resorbable polymer. In embodiments, the framework, skeleton or scaffold is formed from one or more resorbable filaments or struts.

In embodiments, the fiducial markers may further comprise a bioactive agent.

In embodiments, the three-dimensional structure of the fiducial marker is formed by 3D printing. In embodiments, the framework, skeleton or scaffold of the three-dimensional structure is formed by 3D printing of a resorbable polymer. In other embodiments, the fiducial marker is molded.

The fiducial markers preferably have a pyrogen level of less than 20 endotoxin units per device, and can be sterilized.

A. Materials

The fiducial markers may comprise permanent and or degradable materials, and more preferably are made completely from degradable materials, excluding the visualization markers which may be permanent or resorbable. In embodiments, the outer region of the fiducial marker, or the scaffold structure of the fiducial marker, is made from a degradable material. In a preferred embodiment, the fiducial markers comprise one or more resorbable polymers, preferably resorbable thermoplastic polymers and copolymers.

The fiducial markers may, for example, be prepared from polymers including, but not limited to, polymers of glycolic acid, lactic acid, 1,4-dioxanone, trimethylene carbonate, 3-hydroxybutyric acid, 4-hydroxybutyric acid, ε-caprolactone, 1,4-butanediol, and succinic acid, and the following polymers: polyglycolic acid, polylactic acid, polydioxanone, polycaprolactone, copolymers of glycolic and lactic acids, such as VICRYL® polymer, MAXON® and MONOCRYL® polymers, and including poly(lactide-co-caprolactones); poly(orthoesters); polyanhydrides; poly(phosphazenes); polyhydroxyalkanoates (PHA's); synthetically or biologically prepared polyesters; polycarbonates; tyrosine polycarbonates; polyamides (including synthetic and natural polyamides, polypeptides, and poly(amino acids)); polyesteramides; poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk (including recombinant silks and silk derivatives and analogs); chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly (lactide), poly(lactide-co-glycolide), or polycaprolactone and copolymers thereof, including random copolymers and block copolymers thereof. Preferably the resorbable polymer or copolymer will be substantially or completely resorbed in less than 6-24 months following implantation.

Blends of polymers, preferably resorbable polymers, can also be used to prepare the fiducial markers. Particularly preferred blends of resorbable polymers include, but are not limited to, blends formed from polymers comprising glycolic acid, lactic acid, 1,4-dioxanone, trimethylene carbonate, 3-hydroxybutyric acid, 4-hydroxybutyric acid, ε-caprolactone, 1,4-butanediol, succinic acid or copolymers thereof.

In a particularly preferred embodiment, the fiducial markers comprise poly-4-hydroxybutyrate (Tepha's P4HB™ polymer, Lexington, MA) or a copolymer thereof, and may in one embodiment be made completely with P4HB or copolymer thereof, excluding the visualization markers. Copolymers include P4HB with another hydroxyacid, such as 3-hydroxybutyrate, and P4HB with glycolic acid or lactic acid monomer. P4HB is a strong, pliable thermoplastic polyester that is biocompatible and resorbable (Williams, et al. Poly-4-hydroxybutyrate (P4HB): a new generation of resorbable medical devices for tissue repair and regeneration, Biomed. Tech. 58(5):439-452 (2013)). Upon implantation, P4HB hydrolyzes to its monomer, and the monomer is metabolized via the Krebs cycle to carbon dioxide and water. In a preferred embodiment, the P4HB homopolymer and copolymers thereof have a weight average molecular weight, Mw, within the range of 50 kDa to 1,200 kDa (by GPC relative to polystyrene) and more preferably from 100 kDa to 600 kDa, and even more preferably 200 kDa to 450 kDa. A weight average molecular weight of the polymer of 50 kDa or higher is preferred for processing and mechanical properties.

In another preferred embodiment, the fiducial markers comprise a polymer comprising at least a diol and a diacid. In a particularly preferred embodiment, the polymer used to prepare the fiducial marker device is poly(butylene succinate) (PBS) wherein the diol is 1,4-butanediol and the diacid is succinic acid. The poly(butylene succinate) polymer may be a copolymer with other diols, other diacids or a combination thereof. For example, the polymer may be a poly (butylene succinate) copolymer that further comprises one or more of the following: 1,3-propanediol, 2,3-butanediol, ethylene glycol, 1,5-pentanediol, glutaric acid, adipic acid, terephthalic acid, malonic acid, methylsuccinic acid, dimethylsuccinic acid, and oxalic acid. Examples of preferred copolymers are: poly(butylene succinate-co-adipate), poly (butylene succinate-co-terephthalate), poly(butylene succinate-co-butylene methylsuccinate), poly(butylene succinate-co-butylene dimethylsuccinate), poly(butylene succinate-co-ethylene succinate) and poly(butylene succinate-co-propylene succinate). The poly(butylene succinate) polymer or copolymer may also further comprise one or more of the following: chain extender, coupling agent, cross-linking agent and branching agent. For example, poly(butylene succinate) or copolymer thereof may be branched, chain extended, or cross-linked by adding one or more of the following agents: malic acid, trimethylol propane, trimesic acid, citric acid, glycerol propoxylate, and tartaric acid. Particularly preferred agents for branching, chain extension, or crosslinking the poly(butylene succinate) polymer or copolymer thereof are hydroxycarboxylic acid units. Preferably the hydroxycarboxylic acid unit has two carboxylic groups and one hydroxyl group, two hydroxyl groups and one carboxyl group, three carboxyl groups and one hydroxyl group, or two hydroxyl groups and two carboxyl groups. In one preferred embodiment, the fiducial marker comprises poly(butylene succinate) comprising malic acid as a branching, chain extending, or cross-linking agent. This polymer may be referred to as poly(butylene succinate) cross-linked or chain-extended with malic acid, succinic acid-1,4-butanediol-malic acid copolyester, or poly(1,4-butylene glycol-co-succinic acid), cross-linked or chain-extended with malic acid. It should be understood that references to malic acid and other cross-linking agents, coupling agents, branching agents and chain extenders include polymers prepared with these agents wherein the agent has undergone further reaction during processing. For example, the agent may undergo dehydration during polymerization. Thus, poly(butylene succinate)-malic acid copolymer refers to a copolymer prepared from succinic acid, 1,4-butanediol and malic acid. In another preferred embodiment, malic acid may be used as a branching, chain-extending or cross-linking agent to prepare a copolymer of poly(butylene succinate) with adipate, which may be referred to as poly[(butylene succinate)-co-adipate] cross-linked or chain-extended with malic acid. As used herein, "poly(butylene succinate) and copolymers" includes polymers and copolymers prepared with one or more of the following: chain extenders, coupling agents, cross-linking agents and branching agents. In a particularly preferred embodiment, the poly(butylene succinate) and copolymers thereof contain at least 70%, more preferably 80%, and even more preferably 90% by weight of succinic acid and 1,4-butanediol units. The polymers comprising diacid and diols, including poly(butylene succinate) and copolymers thereof and others described herein, preferably have a weight average molecular weight (Mw) of 10,000 Da to 400,000 Da, more preferably 50,000 Da to 300,000 Da and even more preferably 100,000 Da to 200,000 Da based on gel permeation chromatography (GPC) relative to polystyrene standards. In a particularly preferred embodiment, the polymers and copolymers have a weight average molecular weight of 50,000 Da to 300,000 Da, and more preferably 75,000 Da to 300,000 Da. In one preferred embodiment, the poly(butylene succinate) or copolymer thereof used to make the device, or a component of the device, has one or more, or all of the following properties: density of 1.23-1.26 g/cm$^3$, glass transition temperature of −31° C. to −35° C., melting point of 113° C. to 117° C., melt flow rate (MFR) at 190° C./2.16 kgf of 2 to 10 g/10 min, and tensile strength of 30 to 60 MPa.

B. Additives

Certain additives may be incorporated into the devices, preferably in the absorbable polymer, copolymer or blends thereof that are used to make the device. These additives may be incorporated during a compounding process subsequent to fabrication of the device. For example, additives may be melt compounded with polymers, or compounded using a solution-based process.

In a preferred embodiment, the additives are biocompatible, and even more preferably the additives are both biocompatible and resorbable.

In one embodiment, the additives may be nucleating agents and/or plasticizers. These additives may be added in sufficient quantity to produce the desired result. In general, these additives may be added in amounts between 1% and 20% by weight. Nucleating agents may be incorporated to increase the rate of crystallization of the polymer, copolymer or blend. Such agents may be used, for example, to facilitate fabrication of the device, and to improve the mechanical properties of the device. Preferred nucleating agents include, but are not limited to, salts of organic acids such as calcium citrate, polymers or oligomers of PHA polymers and copolymers, high melting polymers such as PGA, talc, micronized mica, calcium carbonate, calcium phosphate, ammonium chloride, and aromatic amino acids such as tyrosine and phenylalanine.

Plasticizers that may be incorporated into the compositions for preparing the devices include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydrofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

C. Visualization Markers

The fiducial markers may comprise one or more visualization markers. The visualization markers may comprise permanent materials, degradable materials, or a combination thereof. Preferably, the visualization markers are completely degradable. The visualization markers may be incorporated into the materials that are used to form the outer region of the fiducial marker, one or more parts of, or all of the scaffold structure of the fiducial marker. In a preferred embodiment, the visualization marker is incorporated into a resorbable polymer. In embodiments, the visualization marker is incorporated into a resorbable polymer and incorporated into the fiducial marker in one or more locations.

Suitable visualization markers that can be incorporated into the fiducial markers include visualization markers that can be detected by one or more of the following methods: x-raying, magnetic resonance imaging, computerized tomography, ultrasound, mammography, positron emission tomography, and single-photon emission computed tomography.

In embodiments, the visualization markers are radiopaque materials.

In embodiments, the visualization markers comprise one or more of the following: titanium, stainless steel, tungsten, barium, zinc, zirconium, strontium, ytterbium, gold, and bismuth. In embodiments, the visualization markers are one or more of the following: barium sulfate, iodinated compounds, bismuth compounds, zinc oxide, zirconium dioxide, titanium dioxide, iodoform, an iodinated compound, bismuth oxide, bismuth subcarbonate, bismuth oxychloride, ytterbium trifluoride, strontium carbonate.

In embodiments, the visualization markers are wires, clips, metals, alloys, ceramics, or powders. Powders that may be incorporated into the fiducial markers include:

titanium, strontium carbonate, zirconium dioxide, barium sulfate, and bismuth (III) oxide.

In embodiments, the visualization markers are composite materials. In embodiments, the visualization markers may be composites of poly hydroxybutyrate or copolymer thereof, or poly(butylene succinate) or copolymer thereof, with a radiopaque material. In embodiments, the visualization markers are composites of poly-4-hydroxybutyrate or copolymer thereof, or poly(butylene succinate) or copolymer thereof with one or more of the following: titanium, stainless steel, tungsten, barium, zinc, zirconium, strontium, ytterbium, gold, bismuth, barium sulfate, iodinated compounds, bismuth compounds, zinc oxide, zirconium dioxide, titanium dioxide, iodoform, bismuth oxide, bismuth subcarbonate, bismuth oxychloride, ytterbium trifluoride, and strontium carbonate. In a preferred embodiment, the visualization marker is a composite of poly-4-hydroxybutyrate or copolymer thereof, or poly(butylene succinate) or copolymer thereof with barium sulfate, zirconium dioxide, or both barium sulfate and zirconium dioxide.

In embodiments, the visualization markers are selected from one or more of the following: fluorescein sodium, iodipamide meglumine, iothalamate meglumine, diatrizoate meglumine, ioflupane i-123, perflutren, diatrizoate sodium, ferumoxsil, gadopentetate dimeglumine, indium in-111 pentetate disodium, gadodiamide, gadoversetamide, gadoxetate disodium, technetium tc-99m gluceptate, gadobenate dimeglumine, albumin human, technetium tc-99m etidronate, technetium tc-99m mertiatide, technetium tc-99m pyrophosphate, technetium tc-99m depreotide, technetium tc-99m fanolesomab, technetium tc-99m ferpentetate, technetium tc-99m albumin, technetium tc-99m gluceptate, technetium tc-99m sestamibi, technetium tc-99m exametazine, technetium tc-99m lidofenin, technetium tc-99m mebrofenin, technetium tc-99m medronate, technetium tc-99m pyrophosphate, technetium tc-99m pentetate, technetium tc-99m disofenin, technetium tc-99m sodium pertechnetate, technetium tc-99m succimer, technetium tc-99m tetrofosmin, technetium tc-99m bicisate, technetium tc-99m pyro/trimeta phosphates, technetium tc-99m teboroxime, xenon xe-133, xenon xe-127, gadofosveset trisodium, iobenguane sulfate i-123, ammonia, n-13, florbetapir f-18, technetium tc-99m pentetate, technetium tc-99m sulfur colloid, technetium tc-99m sodium pertechnetate, technetium tc-99m sestamibi, rubidium chloride rb-82, arcitumomab, choline-11, sodium chromate cr-51, ethiodized oil, ferumoxides, fludeoxyglucose f-18, fluorescein sodium, gadobutrol, gadoteridol, gallium citrate ga-67, iothalamate sodium i-125, ioxaglate meglumine, ioxaglate sodium, sodium iodide i-131, indocyanine green, indium in-111 chloride, indium in-111 oxyquinoline, indium in-111 pentetreotide, indocyanine green, iopamidol, albumin iodinated i-125 serum, iohexol, ioversol, ioxilan, iopromide, capromab pendetide, thallous chloride tl-201, nofetumomab, iodixanol, iothalamate sodium, krypton, kr-81m, iodohippurate sodium i-123, rose bengal sodium i-131, mangafodipir trisodium, xenon xe-133, tyropanoate sodium, cyanocobalamin, cyanocobalamin co-57, ferric ammonium citrate, ferrous citrate, fludeoxyglucose, sodium fluoride f-18, gallium citrate ga-67, iodohippurate sodium i-131, dimyristoyl lecithin, perflexane, perflubron, iobenguane sulfate i-131, sodium iodide i-131, calcium metrizoate, meglumine metrizoate, metrizoate magnesium, metrizoate sodium, manganese chloride tetrahydrate, imciromab pentetate, iophendylate, simethicone-cellulose, and pentetate calcium trisodium yb-169. Additional examples of suitable visualization markers are listed in Savitt et al. 1987, The radiopacity of ingested medications, Ann. Emerg. Med., 16(3):331-9.

In embodiments, the devices are coated to improve their visibility or the visualization markers are coated to improve their visibility. In embodiments, the devices comprise hydrogels to improve their visibility. Hydrogels may be coated on the devices or on the visualization markers of the devices. Suitable hydrogels may be physically or chemically crosslinked. Preferably the hydrogels are absorbable. In embodiments, the hydrogels comprise polysaccharides. In embodiments, the hydrogels comprise hyaluronic acid, alginate, for example, sodium or calcium alginate, collagen, gelatin, fibrin, pectin, Matrigel, and chitosan, or derivatives thereof. In embodiments, the hydrogels are derived from one or more of the following: poly(ethylene oxide), poly(vinyl alcohol), poly(lactic acid) and poly(propylene fumarate). Other examples of hydrogels include poly(ethylene glycol) diacrylate, and poly(acrylamide).

In embodiments, visualization markers comprising titanium, stainless steel, tungsten, barium, zinc, zirconium, strontium, ytterbium, gold, bismuth, barium sulfate, iodinated compounds, bismuth compounds, zinc oxide, zirconium dioxide, titanium dioxide, iodoform, bismuth oxide, bismuth subcarbonate, bismuth oxychloride, ytterbium trifluoride, and strontium carbonate are coated with a hydrogel, and may also further comprise an absorbable polymer, for example, poly-4-hydroxybutyrate or copolymer thereof, or poly(butylene succinate) or copolymer thereof.

C. Bioactive Agents

The fiducial marker devices can be loaded or coated with bioactive agents. Bioactive agents may be included in the devices for a variety of reasons. For example, bioactive agents may be included in order to improve tissue in-growth into the device, to improve tissue maturation, to provide for the delivery of an active agent, to improve wettability of the implant, to prevent infection, and to improve cell attachment. In embodiments, the bioactive agents may also be incorporated into different regions of the device in different concentrations.

In other embodiments, the devices may contain cellular adhesion factors, including cell adhesion polypeptides. As used herein, the term "cell adhesion polypeptides" refers to compounds having at least two amino acids per molecule that are capable of binding cells via cell surface molecules. The cell adhesion polypeptides include any of the proteins of the extracellular matrix which are known to play a role in cell adhesion, including fibronectin, vitronectin, laminin, elastin, fibrinogen, collagen types I, II, and V, as well as synthetic peptides with similar cell adhesion properties. The cell adhesion polypeptides also include peptides derived from any of the aforementioned proteins, including fragments or sequences containing the binding domains.

The devices can incorporate wetting agents designed to improve the wettability of the surfaces of the device to allow fluids to be easily adsorbed onto the device surfaces and into porous devices, and to promote cell attachment and or modify the water contact angle of the device surface. Examples of wetting agents include polymers of ethylene oxide and propylene oxide, such as polyethylene oxide, polypropylene oxide, or copolymers of these, such as PLURONICS®. Other suitable wetting agents include surfactants or emulsifiers.

The devices may contain gels, hydrogels or living hydrogel hybrids to further improve wetting properties and to promote cellular growth throughout the thickness or diameter of the device. Hydrogel hybrids consist of living cells encapsulated in a biocompatible hydrogel like gelatin, silk gels, and hyaluronic acid (HA) gels.

The devices may contain active agents designed to stimulate cell in-growth, including growth factors, cellular differentiating factors, cellular recruiting factors, cell receptors, cell-binding factors, cell signaling molecules, such as cytokines, and molecules to promote cell migration, cell division, cell proliferation and extracellular matrix deposition. Such active agents include fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1-B (IL-1 B), interleukin-8 (IL-8), and nerve growth factor (NGF), and combinations thereof.

Other bioactive agents that can be incorporated in the devices include antimicrobial agents, in particular antibiotics, disinfectants, oncological agents, anti-scarring agents, anti-inflammatory agents, anesthetics, small molecule drugs, anti-angiogenic factors and pro-angiogenic factors, immunomodulatory agents, and blood clotting agents. The bioactive agents may be proteins such as collagen and antibodies, peptides, polysaccharides such as chitosan, alginate, hyaluronic acid and derivatives thereof, nucleic acid molecules, small molecular weight compounds such as steroids, inorganic materials such as hydroxyapatite, or complex mixtures such as platelet rich plasma. Suitable antimicrobial agents include: bacitracin, biguanide, triclosan, gentamicin, minocycline, rifampin, vancomycin, cephalosporins, copper, zinc, silver, and gold. Nucleic acid molecules may include DNA, RNA, siRNA, miRNA, antisense or aptamers.

In a preferred embodiment, bioactive agents are selected from one or more of the following: chemotherapeutic agent, anti-neoplastic agent, immunomodulator, hormonal agent, anti-angiogenesis agent, antibiotic, radiosensitizer, and an immune-therapeutic agent.

In yet another preferred embodiment, the devices may incorporate systems for the controlled release of therapeutic or prophylactic agents.

III. Methods of Manufacturing Fiducial Marker Devices

A variety of methods can be used to manufacture the fiducial marker devices, and several different examples are described herein.

The devices may eliminate or reduce pain that is felt by the patient during their normal daily activities when more rigid fiducial marker devices are implanted in the breast. In contrast to more rigid fiducial markers that are implanted in the breast, the devices described herein are not palpable when implanted in the breast or other tissues, or become so after implantation, and can deform when stress is applied and recover their shape when stress is removed.

The devices also reduce or eliminate the possibility that clinicians unaware of the device will order unnecessary procedures to characterize a foreign body in the patient. Unlike existing partially resorbable or slowly resorbing devices, the devices disclosed herein resorb much faster, and can be produced with visualization markers that allow the entire device to be resorbable.

The devices disclosed herein, unlike existing devices, may also incorporate scaffolds designed to encourage tissue in-growth throughout the void space of a tumor resection cavity. Tissue in-growth not only helps to secure the device in place, but serves as a void filler and helps to prevent the accumulation of fluid in the cavity post-surgery. By promoting tissue in-growth and resorbing relatively fast, the devices can provide improved cosmetic outcomes for the patient, particularly in the treatment of breast cancer. For example, instead of feeling a hard rigid fiducial marker made from polylactic acid in the breast for many years, tissue in-growth into the fiducial marker scaffold will fill the void space of the tumor resection cavity with tissue that has a natural feel, and the fiducial marker will completely degrade leaving no palpable foreign body.

A. Examples of Fiducial Marker Devices

The fiducial marker devices are designed to mold a tumor resection cavity into a defined target volume for radiation therapy with precisely demarcated tissue margins, and to identify the planning target volume. Molding of a tumor resection cavity into a defined shape can decrease the size of tissue margins around the cavity that need to be irradiated, and can reduce exposure of the patient's healthy tissue to radiation.

In one preferred embodiment, the fiducial marker devices have open porous scaffold structures with predefined shapes that define the peripheral boundary of the devices. The open porous scaffold structures help to encourage tissue in-growth which helps to secure visualization markers in place after implantation. Tissue in-growth can also prevent fluid buildup in the tissue resection cavity, and result in an improved cosmetic outcome, for example, following a lumpectomy.

Figure 1B:
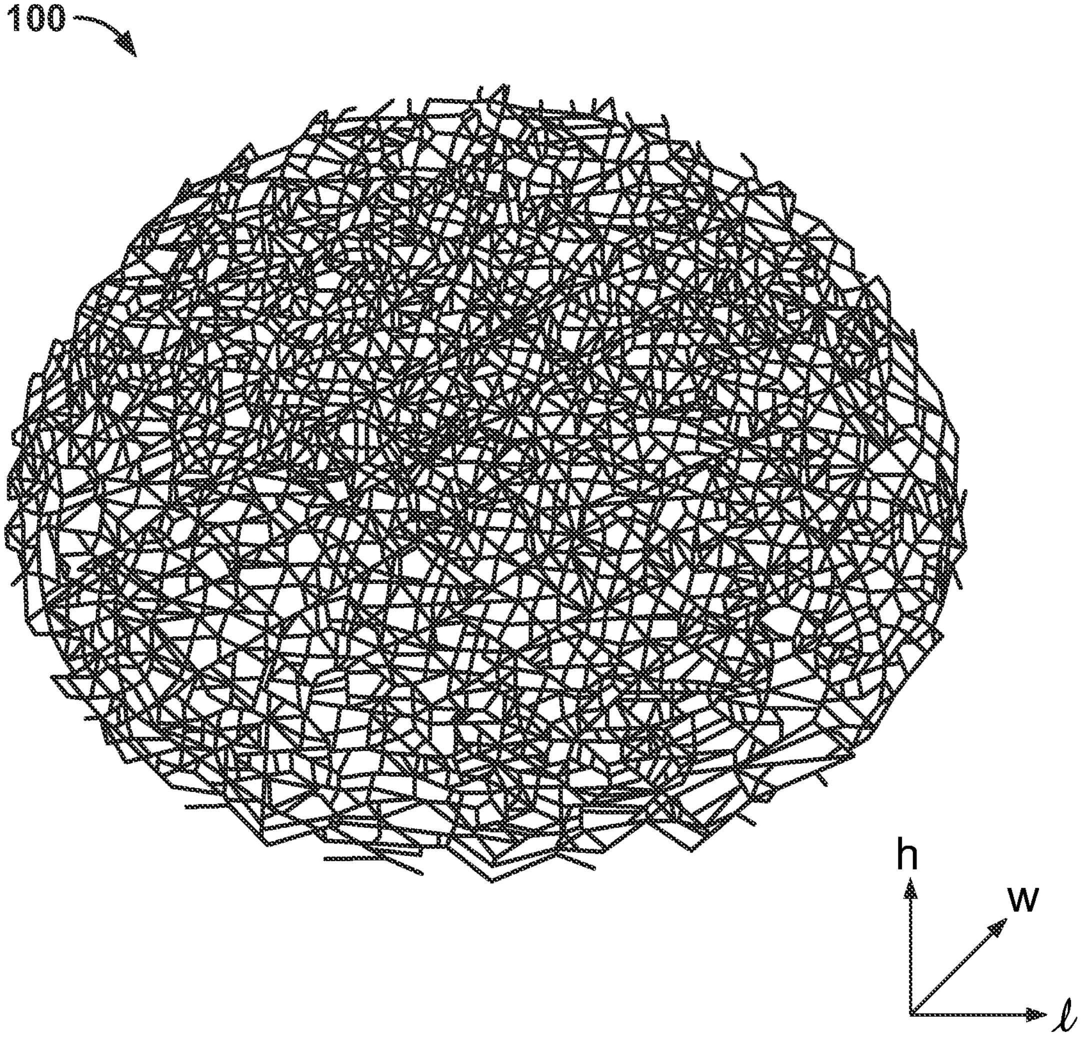

An example of an open porous scaffold structure of a fiducial marker device (100) that is designed to encourage tissue in-growth into the device is show in FIGS. 1A-C. The porous three-dimensional scaffold structure of the marker device (100) has a honeycomb structure formed in an ellipsoid, spherical shape with an outer region defining the peripheral boundary of the device. The scaffold is designed so that the structure of the fiducial marker has a completely interconnected porous architecture. Preferably, the scaffold of the fiducial marker device has a unitary structure. The completely open architecture of the scaffold provides an environment that allows cells to invade the marker device and proliferate following implantation. Tissue in-growth into the honeycomb structure helps to secure the device in place so it will not migrate. Tissue in-growth into the honeycomb structure also allows the device to be used as a void filler. Tissue in-growth helps to reduce or eliminate fluid buildup in the tumor resection cavity post-surgery, and provides an improved cosmetic outcome, for example, in lumpectomy procedures, by reducing or eliminating visible tissue defects. The outer region of the scaffold structure (100) has a predefined shape that is formed by a three-dimensional framework, skeleton or scaffold. The three-dimensional framework, skeleton or scaffold is formed from filaments. The three-dimensional honeycomb framework, skeleton or scaffold (100) of the marker device is able to mold a tissue resection cavity into a defined shape to demarcate the planning target volume for radiation therapy. Molding an irregular shaped tissue resection cavity into the predefined shape of the honeycomb scaffold (100) can decrease the size of tissue margins around the cavity that need to be irradiated, and reduce exposure of healthy patient tissue to radiation. The three-dimensional honeycomb structure (100) of the tissue marker is not rigid, but is rather compressible under stress or tension. Optionally, in embodiments, the three-dimensional honeycomb structure (100) has shape memory. The fiducial marker device (100) has a modulus of elasticity of less than 50 MPa, more preferably less than 1 MPa, and more preferably less than 100 kPa.

These properties allow the predefined shape of the fiducial marker to mold the tissue in the tumor resection cavity into a desirable shape for radiation therapy, but also allow the predefined shape to deform under stress or tension, and recover its predefined shape when the stress or tension is removed. For example, stress or tension from a patient's bra may temporarily deform the predefined shape (100) when the scaffold is implanted in the breast of a patient, but once the bra is removed the scaffold will recover its predefined shape, and any visualization markers placed on the periphery of the scaffold can still be used to accurately demarcate the planning target volume for radiation therapy. This property of the honeycomb structure (100) can eliminate or reduce pain or palpability of the device, particularly when implanted in the breast of a patient. Notably, the predefined shape of the scaffold (100) and its ability to recover its shape after stress or tension is applied and removed, needs only to be retained for the period of radiation therapy or while any visualization markers placed on the periphery of the scaffold are being fixated in place by tissue in-growth. Once radiation therapy is complete or such visualization markers are fixated in place, the scaffold may lose its ability to recover the pre-defined shape and preferably the scaffold is resorbed. Preferably, the scaffold structure is resorbed in less than 6-24 months.

The scaffold of device (100) may be prepared with one or more of the materials disclosed in Section II.A. Preferably, the scaffold (100) is prepared from poly-4-hydroxybutyrate or copolymer thereof or poly(butylene succinate) or copolymer thereof, or comprises one or more of these polymers.

Four constructs with the design of device (100) were prepared from poly-4-hydroxybutyrate by 3D printing. The elastic modulus of each of these devices were measured, and found to be in the range of 0.35 MPa to 0.01 MPa.

Figure 2A:
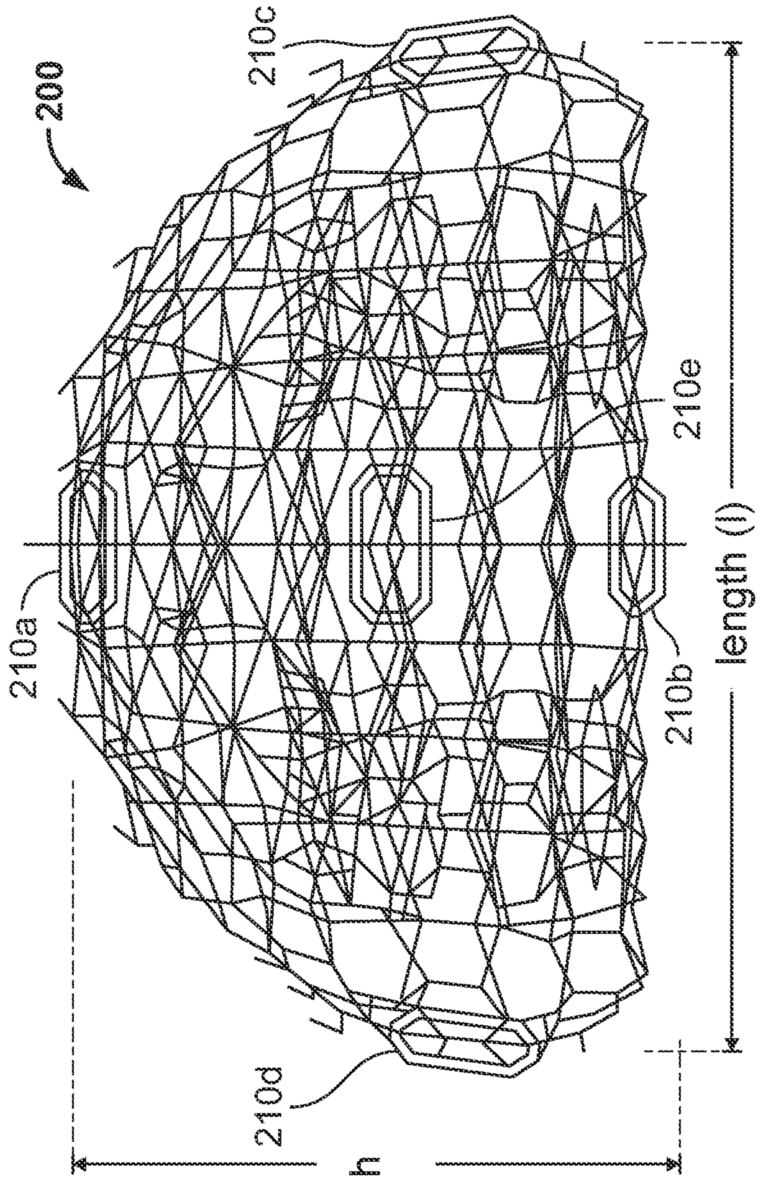
FIGS. 2A-2B show respectively a front view and an isometric view of a porous fiducial marker device (200) with an open porous honeycomb scaffold structure and six titanium clips (210*a-f*) placed on the outer region of the periphery of the structure to allow imaging of the dimensions of the device in accordance with an embodiment of the invention. The device (200) has a base diameter or length (l) and a height (h) shown in FIG. 2A.
Figure 2B:
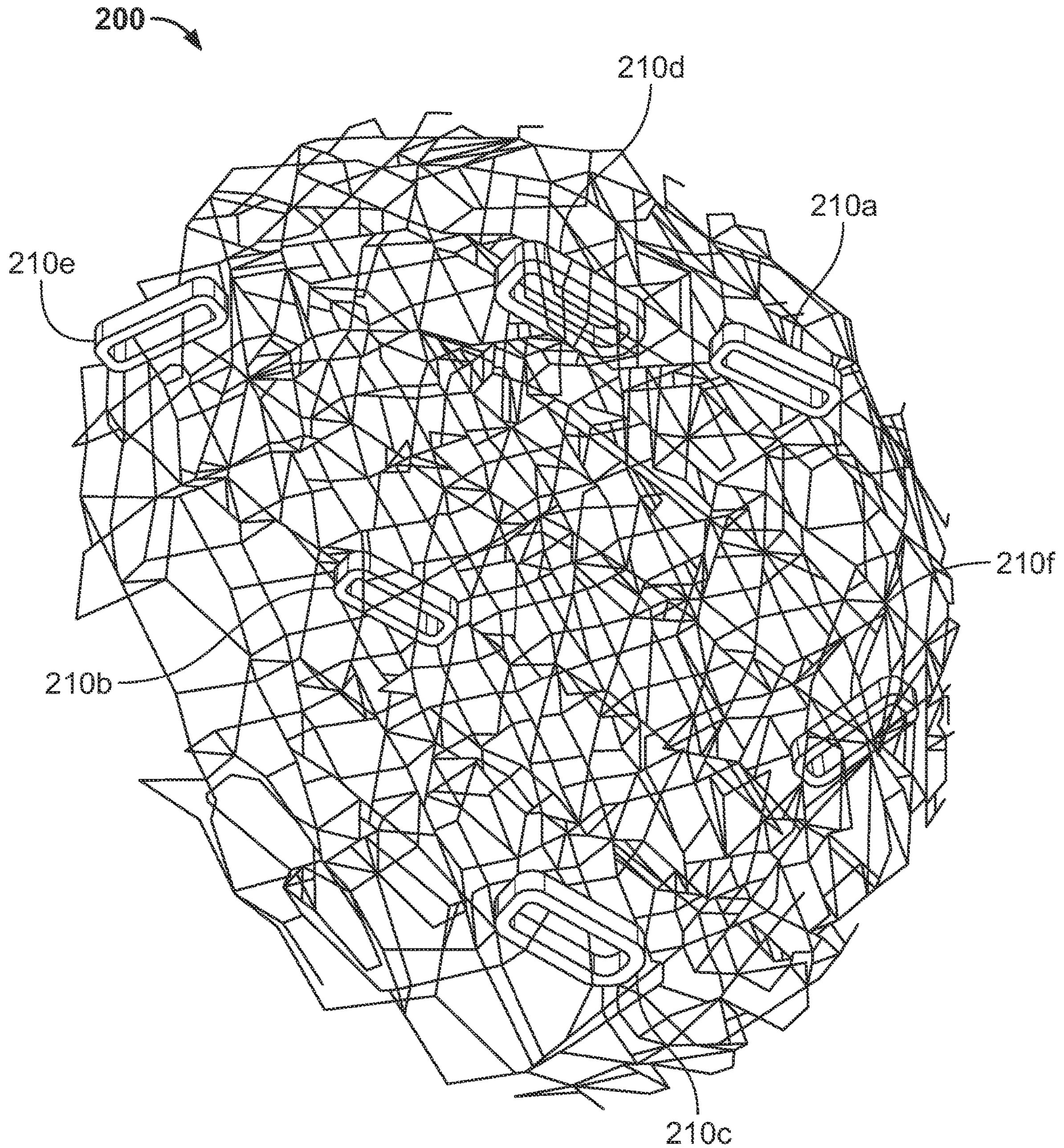

Visualization markers can be incorporated into the filaments of the honeycomb structure of the marker device (100) shown in FIGS. 1A-C. Visualization markers can also be attached to the outer region of the scaffold structure as shown in FIGS. 2A-C. Device (200) is an example of a fiducial marker device formed with the honeycomb open porous scaffold structure shown in FIGS. 1A-C, but with 6 visualization markers (210*a*, 210*b*, 210*c*, 210*d*, 210*e*, 210*f*, collectively referred to as "visualization markers (210)") attached to the outer region of the scaffold structure. A plurality of visualization markers may be attached to the device (200), but preferably six visualization markers are used. The device (200) has an open porous three-dimensional honeycomb scaffold structure with an interconnected porous architecture formed in the shape of an ellipsoid, spherical shape with an outer region defining the peripheral boundary of the device. The open porous scaffold structure encourages cell in-growth and tissue formation which secures the scaffold in place and prevents migration of the scaffold, and importantly, fixates the visualization markers (210) located around the perimeter of the marker device so that they are positioned at the margins of the resected tumor cavity. Tissue in-growth into the device (200) can provide an improved cosmetic outcome by filling a void, such as a void left after a lumpectomy procedure. The fiducial marker (200) has a predefined shape that is formed by a three-dimensional framework, skeleton or scaffold, preferably wherein the framework, skeleton or scaffold is formed from filaments, and the shape is able to mold the shape of a tumor resection cavity into a suitable shape for planning target volume for radiation therapy, but is compressible under stress or tension and will resume its predefined shape when stress or tension is removed. The scaffold of the fiducial marker is designed to maintain its predefined shape, as well as deform under stress and tension, and recover its predefined shape during the period of radiation therapy or the period of time required for the visualization markers (210) to be fixated in place by tissue in-growth into the scaffold. The scaffold is resorbed preferably in less than 9, 10, 11, 12, 13, 14, 15, 16, 17, 18, 19, 20, 21, 22, 23 or 24 months either after radiation therapy has been completed, or once the visualization markers (210) have been fixated in place around the perimeter of the marker device. The scaffold of device (200) may be prepared with one or more of the materials disclosed in Section II.A.

Figure 3A:
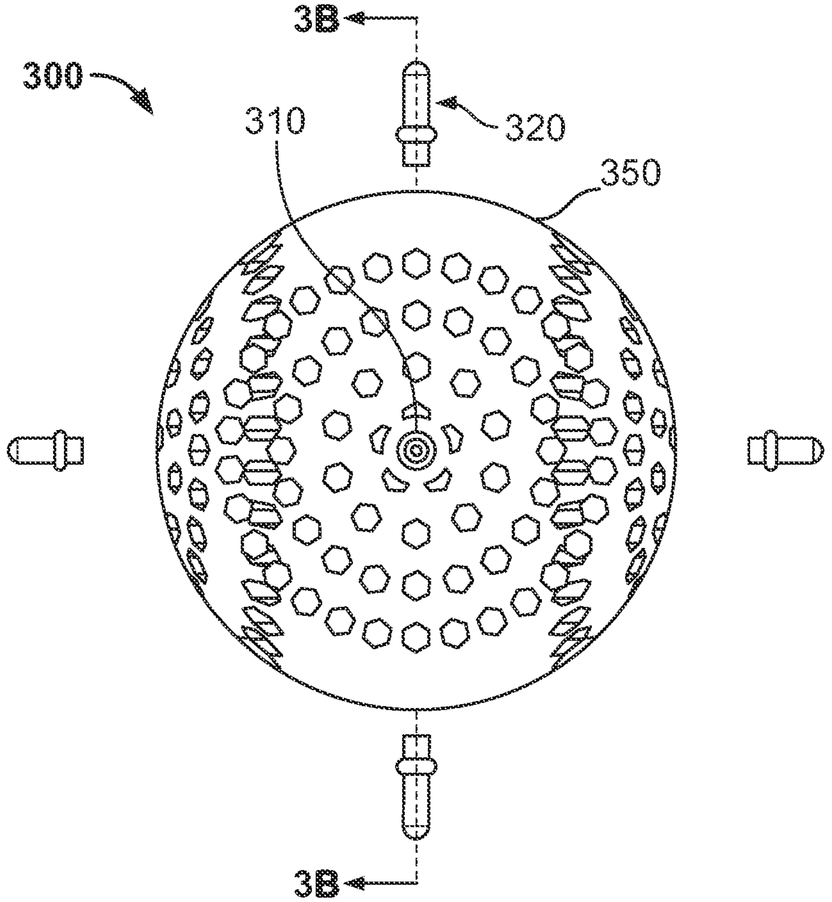
FIG. 3A is an exploded view of a porous resorbable fiducial marker (300) showing a post or pin holder (310) designed to receive a visualization marker which is a radiopaque post or pin (320) in accordance with an embodiment of the invention.

Another example of a fiducial marker device (300) is shown in FIG. 3A. The fiducial marker device (300) has a spherical shaped open porous scaffold structure designed to encourage tissue in-growth with post or pin holders (310) where radiopaque posts or pins (320) can be inserted to form visualization markers on the surface of the device. The implant can comprise an outer surface or peripheral structure (e.g., a shell 350) and an internal organized architecture which can support the peripheral structure and provide an interconnected porous structure or network of pores.

Figure 3B:
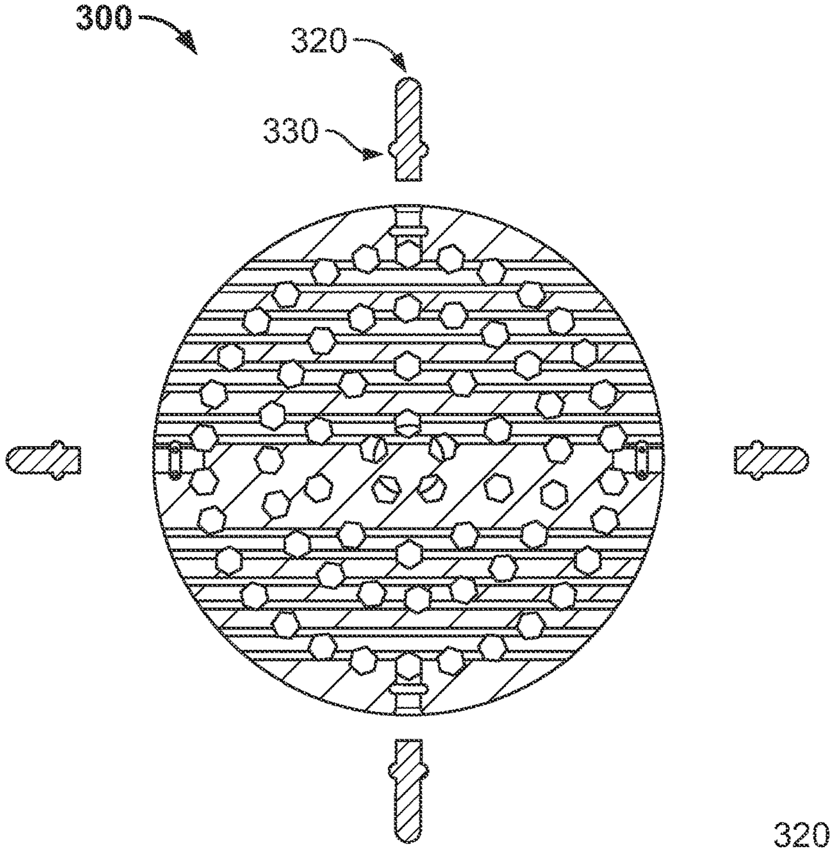
FIG. 3B is a cross-sectional view of the porous resorbable fiducial marker (300) shown in FIG. 3A taken along line "3B-3B."

A cross-section of the device (300) taken along line 3B-3B is shown in FIG. 3B. A locking feature (330) on the radiopaque post/pin (320) is shown in FIG. 3B. The locking feature allows the radiopaque post or pin to be secured on the outer region of the scaffold. Multiple radiopaque posts or pins (320), preferably six, may be positioned on the outer region of the device (300). Appropriate placement of these posts or pins allows the outer region of the device (300) to be imaged for planning target volume and radiation therapy.

In embodiments, visualization markers are located around the perimeter of the device so that the markers are positioned at the margins of the resected tumor cavity. In particular embodiments, visualization markers are placed at the first and second ends of the longitudinal axis of the device so the length (l) of the device can be imaged in vivo. Markers can also be placed around the periphery at the midpoint of the longitudinal axis so the diameter or width of the device can be imaged.

Figure 3C:
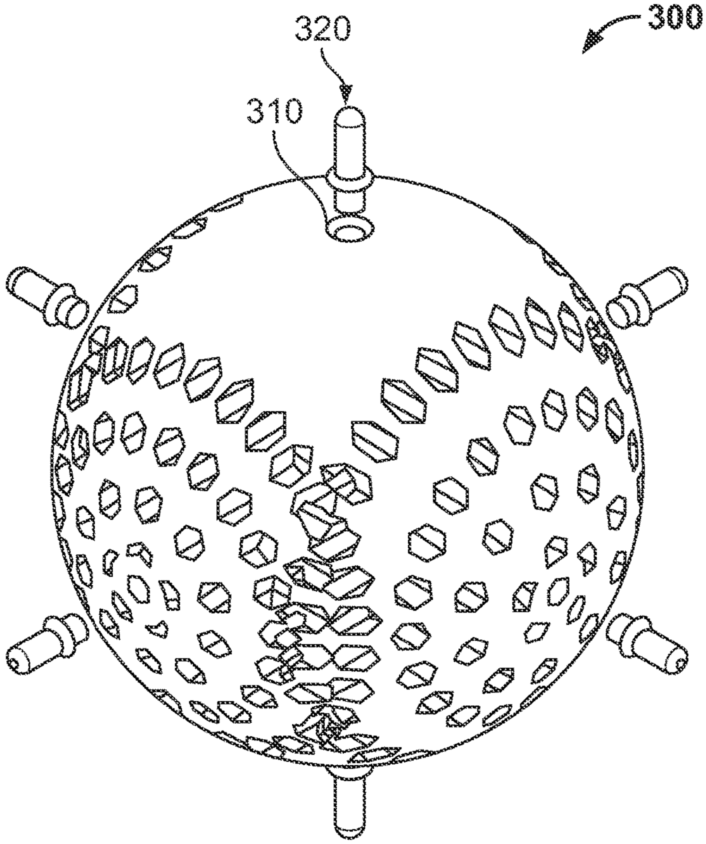
FIG. 3C is a perspective view of the porous resorbable fiducial device (300) shown in FIG. 3A, showing multiple post or pin holders (310) located on the surface of the device, and a radiopaque post or pin (320) above a post or pin holder.

FIG. 3C shows the positions of three post or pin holders (310), located on the outer region of the fiducial marker device (300), where radiopaque posts or pins (320) can be inserted to allow imaging of the device. The device (300) has a unitary structure. The device (300) may be formed with a honeycomb structure or other suitable open porous architecture that provides an environment that allows cells to invade the marker device and proliferate following implantation. Tissue in-growth into the structure (300) helps to secure the device in place so it will not migrate, and to fix the position of visualization markers located around the perimeter of the marker device at the margins of the resected tumor cavity. Tissue in-growth into the structure (300) also allows the device to be used as a void filler, reducing or eliminating fluid buildup in the tumor resection cavity post-surgery, and providing an improved cosmetic outcome, for example, in lumpectomy procedures, by reducing or eliminating visible tissue defects. The outer region of the scaffold structure (300) has a predefined shape that is formed by a three-dimensional framework, skeleton or scaffold. The three-dimensional framework, skeleton or scaffold is formed from filaments. The three-dimensional framework, skeleton or scaffold (300) of the marker device is able to mold a tissue resection cavity into a defined shape to demarcate the planning target volume for radiation therapy. The three-dimensional structure (300) of the tissue marker is not rigid, but is rather compressible under stress or tension. The device (300) has a modulus of elasticity of less than 50 MPa. These properties allow the predefined shape to mold the tissue in the tumor resection cavity into a desirable shape for radiation therapy, but also allow the predefined shape to deform under stress or tension, and recover its predefined shape when the stress or tension is removed. This property of the structure (300) can eliminate or reduce pain or palpability of the device, particularly when implanted in the breast of a patient. Notably, the predefined shape of the scaffold and its ability to recover its shape after stress or tension is applied and removed, needs only to be retained for the period of radiation therapy or while the visualization markers (320) are being fixated in place by tissue in-growth. Once radiation therapy is complete or the visualization markers are fixated in place, the scaffold may lose its ability to recover the pre-defined shape and the scaffold is preferably resorbed. Preferably, the scaffold structure (300) is resorbed in less than 6-24 months. The scaffold of device (300) may be prepared with one or more of the materials disclosed in Section II.A. Preferably, the device (300) is prepared from poly-4-hydroxybutyrate or copolymer thereof or poly(butylene succinate) or copolymer thereof, or comprises one or more of these polymers.

The scaffold structures of the fiducial marker devices may also be 3D printed with other shapes suitable for radiation therapy, including spherical, semi-spherical, spheroid, ellipsoid, cylindrical, parallelepiped shapes, and shapes with convex surfaces. These scaffold structures are formed as open porous structures, and are preferably made by 3D printing of three-dimensional frameworks, skeleton or scaffolds. These frameworks, skeletons or scaffolds may be formed with one or more filaments, and may optionally comprise struts. The frameworks, skeletons or scaffolds may comprise one or more polyhedrons.

B. Dimensions of Fiducial Marker Devices

The fiducial marker devices are sized for use in different sized tumor resection cavities. The fiducial marker devices are sized to define the planning target volume (PTV) for radiation therapy. With reference again to FIGS. 1A, 1B, the devices can be formed in shapes that have a longitudinal axis with a first end, a second end, and length (l) between the first end and the second end. Length (l) is typically from 1 to 6 cm in length, including 1, 2, 3, 4, 5, and 6 cm.

The devices can be formed with a length (l) or width (w) at the midpoint of the longitudinal axis between the first end and the second end. The width (w) at the midpoint of the longitudinal axis of the device is typically from 1 to 5 cm, including 1, 2, 3, 4 and 5 cm. Common sizes of the fiducial marker have dimensions of (l)×(w) of 2×2 cm, 2×3 cm, 3×3 cm, 3×4 cm, 4×4 cm, and 4×5 cm. In embodiments, base area is circular and the length and width are equal to one another.

The devices can also be formed with a longitudinal axis with first and second ends and a length between the first and second ends (l), and a width (w) and height (h) at the midpoint of the longitudinal axis between the first and second ends of the device. Typical values of these dimensions are (l) from 1 to 4 cm, (w) of 1 to 3 cm, and (h) of 1 to 2 cm. Particularly common sizes of fiducial markers with dimensions of length (l)×width (w)×height (h) are 3×2×1 cm, 3×3×1 cm, 1×1×2 cm, 2×1×2 cm, and 1×2×2 cm.

C. Porosities of Fiducial Marker Devices

In embodiments, the open porous scaffold structures of the fiducial marker devices preferably contain macro-pores to encourage cell and tissue in-growth into the interior of the scaffold structure. The macro-pores preferably have average pore size diameters or dimensions of at least 25 microns, more preferably at least 50 microns, and even more preferably at least 75 microns. Average pore size diameters or dimensions may be 0.075 mm to 10 mm. Pore sizes may be different in different regions of the scaffold of the device.

Suitable porous scaffolds of the fiducial marker devices may be formed from hollow or skeletal unit cells. Porous scaffolds with a defined size, shape and volume may be formed by joining hollow or skeletal unit cells together to form the predefined shapes of the three-dimensional fiducial marker devices. These porous fiducial markers can be produced with different shapes and sizes using unit cells of the same or different sizes and shapes. In particularly preferred embodiments, the hollow unit cells and skeletal unit cells are compressible, and even more preferably can recover to their original dimensions after compression. A particularly preferred embodiment is a compressible fiducial marker comprising hollow unit cells or skeletal unit cells that can recover its original dimensions following compression.

The marker devices formed from hollow or skeletal unit cells may comprise 2 or more unit cells, but more preferably 5, 10, 15, 20, 25, 30, 35, 40, 45, 50, 100, 1,000, 10,000 or more unit cells. Unit cells of the scaffold structure of the device may be joined to one or more unit cells that may be of the same type, or a different type. The unit cells forming the scaffold structures of the marker devices may have pores with widths or diameters of 500 μm to 2 cm, and more preferably 1 mm to 1 cm. The unit cells of the devices may have the same pore sizes or a mixture of pore sizes. The fiducial marker devices formed from unit cells preferably have low volumetric densities that provide large surface areas and void volumes. Preferably, the dimensions of the unit cells are selected so that porous scaffolds can be assembled from the unit cells with low volumetric density that can be readily colonized by cells and invaded by tissue and blood vessels.

Different types of fiducial marker scaffolds with different volumetric densities may be produced by appropriate selection of the sizes and shapes of the unit cells. The properties of the scaffolds formed from the repeating unit cells are highly predictable, and can be predicted based on the dimensions of the unit cells, and the materials used to prepare the unit cells. Unit cells with different physical properties may be prepared by selection of the dimensions of the unit cells, geometries of the unit cells, and the material used to prepare the unit cells. Selecting specific unit cell dimensions and materials makes it possible to produce scaffolds from the unit cells with properties that are compressible, yet can be inserted into a tumor resection cavity and conform the tissue margins of the cavity to the predefined shape of the marker device.

The hollow or skeletal unit cells of the porous fiducial devices may be formed from filaments. The lengths of the filaments forming these unit cells are preferably 1 mm to 2 cm, more preferably 2 mm to 1 cm, and even more preferably 3 mm to 9 mm. The lengths of the filaments may be selected to provide devices with specific porosities as well as specific shapes and volumes. The width of the filaments in the unit cells are preferably 500 μm to 2 cm, more preferably 1 mm to 2 cm, and even more preferably 1 mm to 9 mm. One advantage of using unit cells to form the fiducial markers is that filament widths and lengths needed to produce a porous scaffold with a specific elastic modulus or other mechanical property can be calculated for a given material. In embodiments, the mechanical properties of the scaffolds of the fiducial markers may be varied without changing the shape of the unit cells, but instead by varying the dimensions of the filaments of the unit cells. In a preferred embodiment, the porosity, dimensions, and materials of the unit cells forming the scaffolds of the fiducial markers are selected such that the scaffolds prepared from the unit cells have properties that are similar to those of soft tissues. For example, the porosity, dimensions, and materials of the unit cells may be selected to provide scaffold structures that have mechanical properties similar to those of breast tissue. In another preferred embodiment, the unit cells of the fiducial marker device can be compressed, and optionally recover their original shape when the compressive force is released.

The unit cells of the fiducial marker devices may be prepared with one or more of the materials disclosed in Section II.A. Preferably, the unit cells are prepared from compositions comprising poly-4-hydroxybutyrate or copolymer thereof or poly(butylene succinate) or copolymer thereof.

An example of a porous fiducial marker device formed from hollow honeycomb unit cells is shown in FIGS. 1A-C. Other examples of porous fiducial marker devices formed from unit cells include devices formed from skeletal unit cells wherein the unit cells have the shape of polyhedrons.

D. Visualization Markers for Fiducial Marker Devices

The fiducial marker devices are prepared with visualization markers which allow the clinician to use the devices to determine the planning target volume, and to accurately provide radiation treatment to the patient. The visualization markers are located on the outer region of the fiducial marker device in a manner that allows the clinician to image the dimensions of the device in vivo.

The visualization markers may be incorporated into the structure of the outer region of the marker device. For example, a radiopaque material may be used as a visualization marker, and incorporated into filaments of the device that are present in the outer region of the marker device so that the radiopaque material is present at specific discrete locations and not throughout the outer region of the device. Locating the radiopaque material at discrete locations permits subsequent imaging of the interior of the device, which would be compromised or possibly prevented if radiopaque material was incorporated throughout the outer region of the device. Devices made in this manner can be completely resorbable if the radiopaque material is resorbable and the three-dimensional porous structure of the marker device is prepared from resorbable materials. In embodiments, resorbable marker devices can be prepared by incorporating barium sulfate at discrete locations into the outer region of a resorbable porous scaffold structure of a fiducial marker. Preferably, barium sulfate is incorporated at discrete locations into filaments of the outer region of a marker device made from one or more resorbable polymers. For example, a radiopaque material, such as barium sulfate, can be incorporated into discrete locations of the filaments of the honeycomb structure of the marker device (100) shown in FIGS. 1A-C. The barium sulfate may be coated with a hydrogel to improve visualization of the marker.

In other embodiments, visualization markers may be attached to the outer region of a three-dimensional marker device. The visualization markers may, for example, be clasps, clips, or wires made of a radiopaque material that can be attached to the outer region of the device at discrete locations. FIGS. 2A-C show front, side and isometric views of a fiducial marker (200) formed with a honeycomb porous scaffold structure with 6 visualization markers (210) that have been attached to the outer region of the marker's scaffold structure. Any number of visualization markers may be attached to the device (200), but preferably six visualization markers are used.

In other embodiments, the visualization markers may be radiopaque posts or pins that are attached to the outer region of the device. An example of a fiducial marker device with radiopaque posts or pins is shown in FIGS. 3A-C. In this example, the radiopaque posts or pins (320) can be attached to the fiducial marker device at discrete locations by inserting the posts or pins (320) into post or pin holders (310), and fixating them in place using a locking feature (330).

With reference to FIGS. 2A and 2B, in a preferred embodiment, the fiducial marker devices have visualization markers (210*c*, 210*d*) located at the first and second ends of the longitudinal axis of the device. Locating the visualization markers at the first and second ends of the longitudinal axis of the device allows the length (l) of the device to be imaged in vivo. In another preferred embodiment, the fiducial marker devices have visualization markers placed around the periphery of the device at the midpoint of the device's longitudinal axis between the first and second ends of its diameter or width. Preferably, four visualization markers (210*a*, 210*b*, 210*e*, 210*f*) are located around the periphery of the device at its midpoint and two visualization markers (210*c*, 210*d*) are located at the first and second ends of the marker's longitudinal axis. In another embodiment, a visualization marker is placed at each pole of the 3D scaffold, e.g., the north and south pole, and additional visualization markers are placed along one or more latitudes of the 3D body.

In embodiments, the devices may comprise hydrogels. Hydrogels may be used to increase the visibility of the visualization markers. For example, hydrogels may be used in combination with barium sulfate or iodixanol to improve the visualization of the device. The hydrogels may be coated on the visualization markers, or coated on the device.

The fiducial marker devices may comprise visualization markers listed in Section II.C above.

E. Fabrication of Fiducial Marker Devices

In one embodiment, the fiducial marker devices are prepared by 3D printing. Suitable methods for 3D-printing the devices include fused filament fabrication, fused pellet deposition, melt extrusion deposition, selective laser melting, printing of slurries and solutions using a coagulation bath, and printing using a binding solution and granules of powder. Preferably, the devices are prepared by melt extrusion deposition.

In an embodiment, the porous scaffold structure shown in FIGS. 1A-C can be manufactured by melt extrusion deposition from poly-4-hydroxybutyrate (P4HB) using the following procedure. Pellets of P4HB (Mw 380 kDa) may be 3D printed using, for example, an Arburg Freeformer 3D printer, and a 3D CAM (Computer Aided Design Model) for the ellipsoid, spherical shaped, porous honeycomb scaffold structure of the fiducial marker device shown in FIGS. 1A-C. The average diameters of the 3D filaments that are printed are selected based upon the properties of the marker device desired, including the porosity or fill density (i.e. the number of 3D printed filaments per mm between the contours of the 3D printed device). Preferably, the average filament diameters are 50 to 800 μm, more preferably 100 to 600 μm, and even more preferably 150 to 550 μm. 3D Printing of the device is highly desirable since it allows precise control of the shape of the device with an open porous architecture, and the 3D printed structure supports tissue in-growth. 3D Printing is also highly desirable for preparing the devices with shape memory.

Once the fiducial marker scaffold shown in FIGS. 1A-C has been 3D printed, visualization markers may be added to the scaffold to form the device shown in FIGS. 2A-C. Any suitable method may be used to attach the visualization markers to the outer region of the scaffold structure. Preferably, the visualization markers may be clipped, stapled, sewn, or glued onto the scaffold structure.

In other embodiments, fiducial marker devices with radiopaque materials incorporated into discrete locations on the periphery of the device may be produced by 3D printing the devices from combinations of a polymer and a composition comprising a radiopaque material. An exemplary material combination is, without limitation, a polymer containing barium sulfate.

In embodiments, the fiducial marker implants are formed from skeletal polyhedrons with edges and vertices of the unit cells forming the skeletal polyhedron have breaking loads of 0.1 to 200 N, more preferably 1 to 100 N, and even more preferably 2 to 50 N. In embodiments, the edges and vertices of these unit cells have an elongation at break of 22% to 1,000%, and more preferably 100% to 700%. In embodiments, the edges and vertices of these unit cells have an elastic modulus value of 0.05 to 3 GPa, more preferably 0.1 to 1 GPa, and even more preferably 0.2 to 0.8 GPa. The diameters, widths, breaking loads, elongation at break, and elastic modulus values of the edges and vertices of the unit cells may be the same throughout the skeletal polyhedron or unit cells, or these values may be different through the skeletal polyhedron or unit cells. Polymeric struts forming the edges and vertices of the unit cells preferably have one or more of the following properties: (i) breaking load of 0.1 to 200 N, (ii) elongation at break of 22 to 1,000%, and (iii) elastic modulus of 0.05 to 1 GPa. In embodiments, the fiducial marker implants formed from skeletal polyhedron have an elastic modulus of less than 50 MPa, more preferably from 0.1 kPa to 10 MPa, and the polymeric struts or fibers of the unit cells forming the skeletal polyhedron have one or more of the following properties: (i) diameters of 0.025 to 3 mm, more preferably 0.1 to 2 mm, and even more preferably 0.15 to 1 mm; (ii) initial breaking loads of 0.1 to 200 N, more preferably 1 to 100 N, and even more preferably 2 to 50 N; (iii) elongation at break values of 22% to 1,000%, and more preferably 100% to 700%; and (iv) elastic modulus values of 0.05 to 3 GPa, more preferably 0.1 to 1 GPa, and even more preferably 0.2 to 0.8 GPa.

In embodiments, the fiducial marker devices are prepared, for example, by 3D printing, with one or more suture eyelets that can be used during implantation of the device to secure the device and prevent it from migrating. The one or more suture eyelets are preferably located on the periphery of the device.

In embodiments, the fiducial markers may further comprise one or more bioactive agents. These agents may be applied once the porous scaffold structure of the device has been formed, or the bioactive agent may be incorporated into the device during the 3D printing process.

The fiducial marker devices are preferably manufactured with an endotoxin content of less than 20 endotoxin units making them suitable for implantation in a patient.

IV. Methods of Implanting Fiducial Marker Devices

Prior to implantation, the devices are sterilized. The devices may be sterilized, for example, by use of ethylene oxide gas, cold ethylene oxide gas, exposure to gamma-irradiation, or electron-beam irradiation.

While the fiducial markers are particularly well suited and useful for treatment of breast cancer where the devices can be implanted after lumpectomy, the fiducial marker devices may be used in the treatment of other soft tissue cancers, including treatment of liver cancer (for example, treatment of liver tumors), cancer of the muscle (for example, treatment of muscle for sarcoma), abdominal, kidney, lung and prostate cancer. In particular, the devices may be used where tissue is removed from a patient, and the patient may require radiation treatment at or near the site of tissue removal. The fiducial marker devices may also be used at locations in the body where there is a high risk of cancer developing. In these instances, the devices may be used for monitoring the patient, or if cancer subsequently develops for radiation treatment.

The fiducial marker devices may be used by implantation in a tumor bed, or in a surgical resection cavity, and may be imaged prior to the delivery of radiation. The devices may be imaged by one or more of the following techniques: x-raying, magnetic resonance imaging, computerized tomography, ultrasound, mammography, positron emission tomography (PET), or single-photon emission computed tomography (SPECT). Imaging of the device provides a picture of the device that can be used to calculate the planning target volume for radiation therapy, and guide the delivery of radiation to the tumor resection site.

In embodiments, the fiducial markers can be fixated in a tumor bed, or surgical resection cavity, using permanent suture, resorbable suture, staples or by other fixation means. Fixation helps to prevent any subsequent migration of the device until tissue in-growth fixates the device.

In embodiments, the fiducial markers may comprise one or more suture eyelets to fixate the devices in place. Suture may be passed through these eyelets and fixated to tissue in order to prevent migration of the devices after implantation.

In some cancer treatments, multiple radiation doses over a period of days, weeks or months are required. In these instances, the fiducial marker devices may be used to repeatedly identify the tumor resection cavity, and to guide further radiation treatments.

The fiducial marker devices may also be used to deliver one or more bioactive agents in vivo. For example, the fiducial marker may comprise one or more of the following which can be delivered in the vicinity of the implantation site: a chemotherapy agent, an anti-neoplastic agent, an anti-angiogenesis agent, an immunomodulator, a hormonal agent, an immune-therapeutic agent, an antibiotic, and a radio-sensitizing agent.

The fiducial marker devices may also be implanted in tissues to fill voids. In this application, the devices may be used as void fillers. The fiducial marker devices may also be used as markers to assist in radiation treatment, and to fill tissue resection cavities with new tissue. The latter can provide improved cosmetic outcomes, particularly after lumpectomy procedures.

The present invention will be further understood by reference to the following non-limited examples.

EXAMPLES

Example 1: Fiducial Scaffold Markers Made by 3D Printing from poly-4-hydroxybutyrate (P4HB)

Porous fiducial marker devices were made from pellets of P4HB (Mw 380 kDa) by 3D printing. P4HB filaments were deposited layer-by-layer using melt extrusion deposition with the conditions shown in Table 1. The open porous scaffold structures of the devices were formed with a honeycomb structure as shown in FIGS. 1A-B. The structures had an ellipsoid, spherical shape with the length (l) of the structures ranging from 2-6 cm, and a height (h) ranging from 2-8 cm. The devices were formed with completely interconnected porous architectures with open porosity to provide a morphology that allows cells to invade the scaffold and proliferate post-implantation. The fiducial marker devices prepared according to Example 1 had elastic modulus values of 0.01 MPa to 0.35 MPa.

In embodiments, the length (l) equals the width (w) forming a substantially circular base area, in which case the length or width can also be referred to as a base diameter.

Example 2: Clips for Fiducial Markers Prepared from poly-4-hydroxybutyrate and barium sulfate or poly-4-hydroxybutyrate and zirconium dioxide Visualization marker clips suitable for attaching to fiducial marker scaffolds, such as the scaffold prepared in Example 1, may be prepared by injection molding a composition comprising poly-4-hydroxybutyrate and barium sulfate or poly-4-hydroxybutyrate and zirconium dioxide microparticles. Alternatively, the clip may be formed from an acetone solution of poly-4-hydroxybutyrate and barium sulfate or an acetone solution of poly-4-hydroxybutyrate with zirconium dioxide.

Example 3: Fiducial Markers Made from poly-4-hydroxybutyrate (P4HB) by 3D Printing with Barium Sulfate Clip Visualization Markers Six poly-4-hydroxybutyrate clips containing barium sulfate prepared in Example 2 were placed on the outer region of the periphery of the honeycomb scaffold structure prepared in Example 1 at the locations shown in FIGS. 2A-C to allow imaging of the dimensions of the fiducial marker device.

Example 4: Fiducial Markers Made from poly-4-hydroxybutyrate (P4HB) by 3D Printing with Titanium Clip Visualization Markers A porous fiducial marker device was made from P4HB (Mw 380 kDa) using melt extrusion deposition. P4HB filaments were deposited layer-by-layer to form an open porous scaffold with a honeycomb structure. Six titanium clips were then placed on the outer region of the periphery of the honeycomb scaffold structure in locations to allow imaging of the dimensions of the device as shown in FIGS. 2A-C.

We claim:

1. An implantable fiducial tissue marker device comprising:

a resorbable porous scaffold with a three dimensional predefined shape and defining a periphery of the device, wherein the resorbable porous scaffold has shape memory to form the three dimensional predefined shape when the resorbable porous scaffold is not constrained, and a plurality of visualization markers arranged in discrete locations on the periphery of the device, wherein the resorbable porous scaffold comprises connected unit cells, and wherein the unit cells are skeletal polyhedrons.

2. An implantable fiducial tissue marker device comprising a resorbable porous scaffold with a 3D predefined shape and defining a periphery of the device, wherein the resorbable porous scaffold comprises a plurality of visualization markers arranged in discrete locations on the periphery of the device, and wherein the resorbable porous scaffold has a modulus of elasticity of less than 50 MPa, wherein the resorbable porous scaffold comprises connected unit cells, and wherein the unit cells are skeletal polyhedrons.

3. The device of claim 1, wherein the resorbable porous scaffold has a modulus of elasticity greater than 0.5 kPa, and less than 50 MPa.

4. The device of claim 1, wherein the resorbable porous scaffold comprises polymeric struts, fibers, coils or springs that have one or more of the following properties: (i) diameters of 0.025 to 3 mm, 0.1 to 2 mm, or 0.15 to 1 mm; (ii) breaking loads of 0.1 to 200 N, 1 to 100 N, or 2 to 50 N; (iii) elongation at break of 22% to 1,000%, or 100% to 700%; and (iv) elastic modulus values of 0.05 to 3 GPa, or 0.2 to 0.8 GPa.

5. The device of claim 1, wherein the visualization markers are resorbable.

6. The device of claim 1, wherein when the device is implanted in a patient's breast, the device is not palpable immediately after implantation, or within 1, 2, 3, 4, 5 or 6 months of implantation.

7. The device of claim 1, wherein edges and vertices of the skeletal polyhedrons are formed from polymeric struts or fibers.

8. The device of claim 7, wherein the edges and vertices of the unit cells have one or more of the following properties: breaking loads of 0.1 to 200 N, 1 to 100 N, or 2 to 50 N; elongation at break of 22% to 1,000% or 100% to 700%; and elastic modulus value of 0.05 to 3 GPa, 0.1 to 3 GPa, or 0.2 to 0.8 GPa.

9. The device of claim 1, wherein the device has a longitudinal axis with a first end, a second end, and a midpoint between the first and second ends, and wherein the visualization markers are located at the first and second ends of the longitudinal axis, and around the periphery of the device at the midpoint of the device, and the resorbable porous scaffold comprises marker holders for securing the visualization markers in said discrete locations.

10. The device of claim 1, wherein the device is configured to maintain maintains its predefined shape in the absence of stress for at least 1, 2, 3, 4, 5, or 6 months following implantation of the device.

11. The device of claim 1, wherein the resorbable porous scaffold is configured to be resorbed in less than 24, 23, 22, 21, 20, 19, 18, 17, 16, 15, 14, 13, 12, 11, 10, 9, 8, or 7 months following implantation.

12. The device of claim 1, wherein the device further comprises one or more suture eyelets.

13. The device of claim 1, wherein the device further comprises one or more of: a bioactive agent, a hydrogel, hyaluronic acid or derivative thereof, or an alginate.

14. The device of claim 13, wherein the bioactive agent is selected from one or more of the following: chemotherapeutic agent, anti-neoplastic agent, immunomodulator, hormonal agent, anti-angiogenesis agent, antibiotic, radiosensitizer, and an immune-therapeutic agent.

15. The device of claim 1, wherein the periphery of the device defined by the three dimensional predefined shape is spherical, ellipsoid, cylindrical, spheroidal, parallelepiped, oval or is convex.

16. The device of claim 1, wherein the visualization markers can be detected by one or more of the following techniques: x-raying, magnetic resonance imaging, computerized tomography, ultrasound, mammography, positron emission tomography, and single-photon emission computed tomography.

17. The device of claim 1, wherein the device comprises a resorbable polymer.

18. The device of claim 17, wherein the device comprises an oriented resorbable polymer.

19. The device of claim 17, wherein the resorbable polymer is poly-4-hydroxy butyrate or copolymer thereof, or poly(butylene succinate) or copolymer thereof.

20. The device of claim 1, wherein the device comprises one or more sections, or clips, of a radiopaque fiber or a radiopaque strut.

21. The device of claim 7, wherein the device is formed by a process comprising forming the unit cells of the resorbable porous scaffold by three dimensional printing of the fiber or struts.

22. The device of claim 21, wherein the device is formed by one of the following methods: melt extrusion deposition, fused filament fabrication, fused pellet deposition, selective laser melting, printing of a polymer slurry or solution using a coagulation bath, and printing using a binding solution and granules of polymer powder.

23. The device of claim 22, wherein the device is formed from poly-4-hydroxy butyrate or copolymer thereof, or poly(butylene succinate) or copolymer thereof.

24. A method of implanting a fiducial marker device comprising:

creating a surgical site including a cavity in a patient by removing soft tissue through an open surgical incision from a location within a body of the patient;

inserting, into the cavity, a fiducial marker device having a resorbable porous scaffold with a predefined shape defining a periphery of the device, wherein the predefined shape has shape memory, and wherein the resorbable porous scaffold comprises connected unit cells, and wherein the unit cells are skeletal polyhedrons; and closing the surgical site.

25. A physician customizable fiducial marker kit comprising:

at least one fiducial marker device comprising a three dimensional body, and a plurality of fixed, spaced-apart, visualization marker engagement features, wherein the three dimensional body includes a porous scaffold comprising connected unit cells, and wherein the unit cells are skeletal polyhedrons; and a plurality of visualization markers, each comprising a locking feature formed on the visualization marker and configured to mechanically engage with said visualization marker engagement features such that one or more of said visualization markers may be secured to the three dimensional body of the fiducial marker device as desired by the physician.

26. An implantable fiducial tissue marker device comprising:

a shell having an outer peripheral surface;

an internal organized architecture positioned interior to the shell and adapted to support the shell; and a plurality of visualization markers arranged at discrete locations on the peripheral surface of the shell, wherein the internal organized architecture is a resorbable porous scaffold with a three dimensional predefined shape, wherein the resorbable porous scaffold comprises connected unit cells, and wherein the unit cells are skeletal polyhedrons.

27. The physician customizable fiducial marker kit of claim 25, wherein the locking feature and the visualization marker engagement feature are configured to mechanically interlock with one another.

28. The method of claim 24, wherein edges and vertices of the skeletal polyhedrons are formed from polymeric struts or fibers.

29. The method of claim 24, wherein the fiducial marker device comprises an oriented resorbable polymer.

30. The method of claim 29, wherein the oriented resorbable polymer is poly-4-hydroxy butyrate or copolymer thereof, or poly(butylene succinate) or copolymer thereof.

31. The method of claim 24, wherein the fiducial marker device includes a plurality of visualization markers arranged in discrete locations on a three dimensional body of the fiducial marker device.

32. The method of claim 31, further comprising mechanically engaging locking features of the plurality of visualization markers with visualization marker engagement features to secure the plurality of visualization markers to the three dimensional body.

33. The method of claim 31, wherein the plurality of visualization markers are resorbable.

* * * * *